US006821749B1

(12) United States Patent
Kajiwara et al.

(10) Patent No.: US 6,821,749 B1
(45) Date of Patent: Nov. 23, 2004

(54) METHODS OF PRODUCING CAROTENOIDS USING DNA MOLECULES ENCODING ISOPENTENYL PYROPHOSPHATE ISOMERASE

(75) Inventors: Susumu Kajiwara, Tokyo (JP); Norihiko Misawa, Yokohama (JP); Keiji Kondo, Yokohama (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 08/737,319

(22) PCT Filed: Mar. 8, 1996

(86) PCT No.: PCT/JP96/00574
§ 371 (c)(1),
(2), (4) Date: Nov. 12, 1996

(87) PCT Pub. No.: WO96/28545
PCT Pub. Date: Sep. 19, 1996

(30) Foreign Application Priority Data

Mar. 10, 1995 (JP) .............................................. 7-051234

(51) Int. Cl.⁷ ................................................ C12P 23/00
(52) U.S. Cl. ...................... 435/67; 536/23.1; 536/23.2; 536/23.6; 536/23.74; 435/233
(58) Field of Search ...................... 435/67, 233, 320.1, 435/325, 252.3, 254.11, 419, 252.33, 254.3; 536/23.1, 23.2, 23.74, 23.6

(56) References Cited

U.S. PATENT DOCUMENTS

| | | | | |
|---|---|---|---|---|
| 5,356,810 A | * | 10/1994 | Fleno et al. | 435/225.1 |
| 5,744,341 A | * | 4/1998 | Cunningham et al. | 435/189 |
| 6,329,141 B1 | * | 12/2001 | Van Ooijen et al. | |
| 6,524,811 B1 | * | 2/2003 | Cunningham et al. | 435/67 |
| 6,642,021 B2 | * | 11/2003 | Cunningham et al. | 435/67 |

FOREIGN PATENT DOCUMENTS

| | | |
|---|---|---|
| EP | 0 393 690 | 10/1990 |
| EP | WO 97/23633 | * 12/1996 |
| JP | WO 96/28545 | * 9/1996 |
| WO | 97/23633 | 7/1997 |
| WO | WO 97/36998 | * 10/1997 |
| WO | WO 99/63055 | * 12/1999 |

OTHER PUBLICATIONS

Albrecht et al. Light–Stimulated Carotenoid Biosynthesis during Transformation of Maize Etioplasts Is Regulated by Increased Activity of Isopentenyl Pyrophosphate Isomerase. Plant Physiology (1994) 105:529–534.*
GenBank Accession No. X82627, C. breweri mRNA for isopentenyl pyrophosphate isomerase. Nov., 1994.*
Goodwin "Biosynthesis of Carotenoids: An Overview" Methods in Enzymology vol. 214, pp. 330–340, 1993.*
Yamano et al., "Metabolic Engineering for Production of B–Carotene and Lycopene in Saccharomyces", Biosci. Biotech. Biochem., vol. 58, No. 6, (1994) pp. 1112–1114.
Anderson et al., "Isopentenyl Diphosphate:Dimethylallyl Diphosphate Isomerase", The Journal of Biological Chemistry, vol. 264, No. 32, (1989) pp. 19169–19169.
Misawa et al., "Produc. B–Carotene Zymomonas Mobilis Agrobacterium Tumefaciens by Intro. Biosynthesis Genes Erwinia Uredovora", App. & Environ. Microbio., vol. 57, No. 8, (1991) pp. 1847–1849.
Misawa, "The Chemistry of Natural Products", Symposium Papers, (1994).
Matt S. Anderson et al. "Isopentenyl Diphosphate:Dimethylally Diphosphate Isomerase" Journal Biological Chemistry (1989) 264(32) : 19169–19175.
I.P. Street et al., Isopentenyldiphosphate: Dimethylallyldiphosphate Isomerase: Construction of a High–Level Heterologous Expression System for the Gene from Saccharomyces cerevisiae and Identification of an Active–Site Nucleophile: Biochemistry, 1990, vol. 29, p. 7531–7538.

* cited by examiner

Primary Examiner—Kathleen Kerr
(74) Attorney, Agent, or Firm—Foley & Lardner LLP

(57) ABSTRACT

The production of carotenoid is accomplished using a DNA molecule that encodes a polypeptide as obtained from *Haematococcus pluvialis, Phaffia rhodozyma,* or *Saccharomyces cerevisiae,* having isopentonyl pyrophosphate (IPP) isomerase activity, or DNA molecule having a nucleotide sequence that hybridizes thereto. In particular, one can introduce such a DNA molecule into a carotenoid-producing microorganism, culture the microorganism thus transformed, and then obtain carotenoids in the culture broth and cells.

8 Claims, 14 Drawing Sheets

```
              9          18         27         36         45         54
    ATG TCC ATG CCC AAC ATT GTT CCC CCC GCC GAG GTC CGA ACC GAA GGA CTC AGT
    Met Ser Met Pro Asn Ile Val Pro Pro Ala Glu Val Arg Thr Glu Gly Leu Ser
                                                                         18
             63         72         81         90         99        108
    TTA GAA GAG TAC GAT GAG GAG CAG GTC AGG CTG ATG GAG GAG CGA TGT ATT CTT
    Leu Glu Glu Tyr Asp Glu Glu Gln Val Arg Leu Met Glu Glu Arg Cys Ile Leu
                                                                         36
            117        126        135        144        153        162
    GTT AAC CCG GAC GAT GTG GCC TAT GGA GAG GCT TCG AAA AAG ACC TGC CAC TTG
    Val Asn Pro Asp Asp Val Ala Tyr Gly Glu Ala Ser Lys Lys Thr Cys His Leu
                                                                         54
            171        180        189        198        207        216
    ATG TCC AAC ATC AAC GCG CCC AAG GAC CTC CTC CAC CGA GCA TTC TCC GTG TTT
    Met Ser Asn Ile Asn Ala Pro Lys Asp Leu Leu His Arg Ala Phe Ser Val Phe
                                                                         72
            225        234        243        252        261        270
    CTC TTC CGC CCA TCG GAC GGA GCA CTC CTG CTT CAG CGA AGA GCG GAC GAG AAG
    Leu Phe Arg Pro Ser Asp Gly Ala Leu Leu Leu Gln Arg Arg Ala Asp Glu Lys
                                                                         90
            279        288        297        306        315        324
    ATT ACG TTC CCT GGA ATG TGG ACC AAC ACG TGT TGC AGT CAT CCT TTG AGC ATC
    Ile Thr Phe Pro Gly Met Trp Thr Asn Thr Cys Cys Ser His Pro Leu Ser Ile
                                                                        108
            333        342        351        360        369        378
    AAG GGC GAG GTT GAA GAG GAG AAC CAG ATC GGT GTT CGA CGA GCT GCG TCC CGA
    Lys Gly Glu Val Glu Glu Glu Asn Gln Ile Gly Val Arg Arg Ala Ala Ser Arg
                                                                        126
            387        396        405        414        423        432
    AAG TTG GAG CAC GAG CTT GGC GTG CCT ACA TCG TCG ACT CCG CCC GAC TCG TTC
    Lys Leu Glu His Glu Leu Gly Val Pro Thr Ser Ser Thr Pro Pro Asp Ser Phe
                                                                        144
            441        450        459        468        477        486
    ACC TAC CTC ACT AGG ATA CAT TAC CTC GCT CCG AGT GAC GGA CTC TGG GGA GAA
    Thr Tyr Leu Thr Arg Ile His Tyr Leu Ala Pro Ser Asp Gly Leu Trp Gly Glu
                                                                        162
            495        504        513        522        531        540
    CAC GAG ATC GAC TAC ATT CTC TTC TCA ACC ACA CCT ACA GAA CAC ACT GGA AAC
    His Glu Ile Asp Tyr Ile Leu Phe Ser Thr Thr Pro Thr Glu His Thr Gly Asn
                                                                        180
            549        558        567        576        585        594
    CCT AAC GAA GTC TCT GAC ACT CGA TAT GTC ACC AAG CCC GAG CTC CAG GCG ATG
    Pro Asn Glu Val Ser Asp Thr Arg Tyr Val Thr Lys Pro Glu Leu Gln Ala Met
                                                                        198
```

FIG.5

```
         603         612         621         630         639         648
TTT GAG GAC GAG TCT AAC TCA TTT ACC CCT TGG TTC AAG TTG ATT GCC CGA GAC
Phe Glu Asp Glu Ser Asn Ser Phe Thr Pro Trp Phe Lys Leu Ile Ala Arg Asp
                                                                     216
         657         666         675         684         693         702
TTC CTG TTT GGC TGG TGG GAT CAA CTT CTC GCC AGA CGA AAT GAA AAG GGT GAG
Phe Leu Phe Gly Trp Trp Asp Gln Leu Leu Ala Arg Arg Asn Glu Lys Gly Glu
                                                                     234
         711         720         729         738         747         756
GTC GAT GCC AAA TCG TTG GAG GAT CTC TCG GAC AAC AAA GTC TGG AAG ATG TAG
Val Asp Ala Lys Ser Leu Glu Asp Leu Ser Asp Asn Lys Val Trp Lys Met ***
                                                                     251
```

```
          9           18          27          36          45          54
ATG CAG CTG CTT GCC GAG GAC CGC ACA GAC CAT ATG AGG GGT GCA AGT ACC TGG
Met Gln Leu Leu Ala Glu Asp Arg Thr Asp His Met Arg Gly Ala Ser Thr Trp
                                                                      18
          63          72          81          90          99         108
GCA GGC GGG CAG TCG CAG GAT GAG CTG ATG CTG AAG GAC GAG TGC ATC TTG GTG
Ala Gly Gly Gln Ser Gln Asp Glu Leu Met Leu Lys Asp Glu Cys Ile Leu Val
                                                                      36
         117         126         135         144         153         162
GAT GCT GAC GAC AAC ATT ACA GGC CAT GTC AGC AAG CTG GAG TGC CAC AAG TTC
Asp Ala Asp Asp Asn Ile Thr Gly His Val Ser Lys Leu Glu Cys His Lys Phe
                                                                      54
         171         180         189         198         207         216
CTA CCA CAT CAG CCT GCA GGC CTG CTG CAC CGG GCC TTC TCT GTA TTC CTG TTT
Leu Pro His Gln Pro Ala Gly Leu Leu His Arg Ala Phe Ser Val Phe Leu Phe
                                                                      72
         225         234         243         252         261         270
GAC GAC CAG GGG CGA CTG CTG CTG CAA CAG CGT GCA CGA TCA AAA ATC ACA TTC
Asp Asp Gln Gly Arg Leu Leu Leu Gln Gln Arg Ala Arg Ser Lys Ile Thr Phe
                                                                      90
         279         288         297         306         315         324
CCC AGT GTG TGG ACC AAC ACC TGC TGC AGC CAC CCT CTA CAT GGG CAG ACC CCA
Pro Ser Val Trp Thr Asn Thr Cys Cys Ser His Pro Leu His Gly Gln Thr Pro
                                                                     108
         333         342         351         360         369         378
GAT GAG GTG GAC CAA CTA AGC CAG GTG GCC GAC GGC ACA GTA CCT GGC GCA AAG
Asp Glu Val Asp Gln Leu Ser Gln Val Ala Asp Gly Thr Val Pro Gly Ala Lys
                                                                     126
         387         396         405         414         423         432
GCT GCT GCC ATC CGC AAG TTG GAG CAC GAG CTG GGG ATA CCA GCG CAC CAG CTG
Ala Ala Ala Ile Arg Lys Leu Glu His Glu Leu Gly Ile Pro Ala His Gln Leu
                                                                     144
         441         450         459         468         477         486
CCG GCC AGC GCG TTT CGC TTC CTC ACG CGT TTG CAC TAC TGC GCC GCG GAC GTG
Pro Ala Ser Ala Phe Arg Phe Leu Thr Arg Leu His Tyr Cys Ala Ala Asp Val
                                                                     162
         495         504         513         522         531         540
CAG CCG GCT GCG ACA CAA TCA GCA CTC TGG GGC GAG CAC GAA ATG GAC TAC ATC
Gln Pro Ala Ala Thr Gln Ser Ala Leu Trp Gly Glu His Glu Met Asp Tyr Ile
                                                                     180
         549         558         567         576         585         594
TTA TTC ATC CGG GCC AAC GTC ACC CTT GCG CCC AAC CCT GAC GAG GTG GAC GAA
Leu Phe Ile Arg Ala Asn Val Thr Leu Ala Pro Asn Pro Asp Glu Val Asp Glu
                                                                     198
```

FIG.7

```
        603         612         621         630         639         648
GTC AGG TAC GTG ACG CAG GAG GAG CTG CGG CAG ATG ATG CAG CCG GAC AAT GGG
Val Arg Tyr Val Thr Gln Glu Glu Leu Arg Gln Met Met Gln Pro Asp Asn Gly
                                                                    216
        657         666         675         684         693         702
TTG CAA TGG TCG CCG TGG TTT CGC ATC ATC GCC GCG CGC TTC CTT GAG CGC TGG
Leu Gln Trp Ser Pro Trp Phe Arg Ile Ile Ala Ala Arg Phe Leu Glu Arg Trp
                                                                    234
        711         720         729         738         747         756
TGG GCT GAC CTA GAC GCG GCC CTG AAC ACT GAC AAA CAC GAG GAT TGG GGA ACG
Trp Ala Asp Leu Asp Ala Ala Leu Asn Thr Asp Lys His Glu Asp Trp Gly Thr
                                                                    252
        765         774    780
GTG CAT CAC ATC AAC GAA GCG TGA
Val His His Ile Asn Glu Ala ***
                        259↑
                         D
```

FIG. 8

E
↓
```
         9           18          27          36          45          54
ATG ACT GCC GAC AAC AAT AGT ATG CCC CAT GGT GCA GTA TCT AGT TAC GCC AAA
Met Thr Ala Asp Asn Asn Ser Met Pro His Gly Ala Val Ser Ser Tyr Ala Lys
                                                                      18

63          72          81          90          99         108
TTA GTG CAA AAC CAA ACA CCT GAA GAC ATT TTG GAA GAG TTT CCT GAA ATT ATT
Leu Val Gln Asn Gln Thr Pro Glu Asp Ile Leu Glu Glu Phe Pro Glu Ile Ile
                                                                      36

117         126         135         144         153         162
CCA TTA CAA CAA AGA CCT AAT ACC CGA TCT AGT GAG ACG TCA AAT GAC GAA AGC
Pro Leu Gln Gln Arg Pro Asn Thr Arg Ser Ser Glu Thr Ser Asn Asp Glu Ser
                                                                      54

171         180         189         198         207         216
GGA GAA ACA TGT TTT TCT GGT CAT GAT GAG GAG CAA ATT AAG TTA ATG AAT GAA
Gly Glu Thr Cys Phe Ser Gly His Asp Glu Glu Gln Ile Lys Leu Met Asn Glu
                                                                      72

225         234         243         252         261         270
AAT TGT ATT GTT TTG GAT TGG GAC GAT AAT GCT ATT GGT GCC GGT ACC AAG AAA
Asn Cys Ile Val Leu Asp Trp Asp Asp Asn Ala Ile Gly Ala Gly Thr Lys Lys
                                                                      90

279         288         297         306         315         324
GTT TGT CAT TTA ATG GAA AAT ATT GAA AAG GGT TTA CTA CAT CGT GCA TTC TCC
Val Cys His Leu Met Glu Asn Ile Glu Lys Gly Leu Leu His Arg Ala Phe Ser
                                                                     108

333         342         351         360         369         378
GTC TTT ATT TTC AAT GAA CAA GGT GAA TTA CTT TTA CAA CAA AGA GCC ACT GAA
Val Phe Ile Phe Asn Glu Gln Gly Glu Leu Leu Leu Gln Gln Arg Ala Thr Glu
                                                                     126

387         396         405         414         423         432
AAA ATA ACT TTC CCT GAT CTT TGG ACT AAC ACA TGC TGC TCT CAT CCA CTA TGT
Lys Ile Thr Phe Pro Asp Leu Trp Thr Asn Thr Cys Cys Ser His Pro Leu Cys
                                                                     144

441         450         459         468         477         486
ATT GAT GAC GAA TTA GGT TTG AAG GGT AAG CTA GAC GAT AAG ATT AAG GGC GCT
Ile Asp Asp Glu Leu Gly Leu Lys Gly Lys Leu Asp Asp Lys Ile Lys Gly Ala
                                                                     162

495         504         513         522         531         540
ATT ACT GCG GCG GTG AGA AAA CTA GAT CAT GAA TTA GGT ATT CCA GAA GAT GAA
Ile Thr Ala Ala Val Arg Lys Leu Asp His Glu Leu Gly Ile Pro Glu Asp Glu
                                                                     180
```

FIG. 9

```
       549         558         567         576         585         594
ACT AAG ACA AGG GGT AAG TTT CAC TTT TTA AAC AGA ATC CAT TAC ATG GCA CCA
Thr Lys Thr Arg Gly Lys Phe His Phe Leu Asn Arg Ile His Tyr Met Ala Pro
                                                                    198
       603         612         621         630         639         648
AGC AAT GAA CCA TGG GGT GAA CAT GAA ATT GAT TAC ATC CTA TTT TAT AAG ATC
Ser Asn Glu Pro Trp Gly Glu His Glu Ile Asp Tyr Ile Leu Phe Tyr Lys Ile
                                                                    216
       657         666         675         684         693         702
AAC GCT AAA GAA AAC TTG ACT GTC AAC CCA AAC GTC AAT GAA GTT AGA GAC TTC
Asn Ala Lys Glu Asn Leu Thr Val Asn Pro Asn Val Asn Glu Val Arg Asp Phe
                                                                    234
       711         720         729         738         747         756
AAA TGG GTT TCA CCA AAT GAT TTG AAA ACT ATG TTT GCT GAC CCA AGT TAC AAG
Lys Trp Val Ser Pro Asn Asp Leu Lys Thr Met Phe Ala Asp Pro Ser Tyr Lys
                                                                    252
       765         774         783         792         801         810
TTT ACG CCT TGG TTT AAG ATT ATT TGC GAG AAT TAC TTA TTC AAC TGG TGG GAG
Phe Thr Pro Trp Phe Lys Ile Ile Cys Glu Asn Tyr Leu Phe Asn Trp Trp Glu
                                                                    270
       819         828         837         846         855         864
CAA TTA GAT GAC CTT TCT GAA GTG GAA AAT GAC AGG CAA ATT CAT AGA ATG CTA
Gln Leu Asp Asp Leu Ser Glu Val Glu Asn Asp Arg Gln Ile His Arg Met Leu
                                                                    288
867

TAA                                                                   F
***
```

Aa: AatII, A: AccII, B:BssHII, D:DraI, Hi:HincII, H:HpaI, K:KpnI, M:MluI, N:NotI, P:PstI, Sa:SacI, S:SalI, Sp:SphI, X:XbaI

FIG. 14

| E.coli | µg carotene/g dry weight | production ratio |
|---|---|---|
| L: control | 228 | 1 |
| L: pRH1 | 825 | 3.6 |
| L: pHP11 | 1029 | 4.5 |
| L: pSI1 | 859 | 3.8 |
| β: control | 488 | 1 |
| β: pRH1 | 709 | 1.5 |
| P: control | 246 | 1 |
| P: pRH1 | 413 | 1.7 |
| P: pHP11 | 504 | 2.1 |

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 251 amino acids
      (B) TYPE: amino acid
      (D) TOPOLOGY: linear (ii) MOLECULE TYPE: protein (xi) SEQUENCE DESCRIPTION: SEQ ID NO:1:

```
Met Ser Met Pro Asn Ile Val Pro Pro Ala Glu Val Arg Thr Glu Gly
 1               5                  10                  15

Leu Ser Leu Glu Glu Tyr Asp Glu Glu Gln Val Arg Leu Met Glu Glu
                20                  25                  30

Arg Cys Ile Leu Val Asn Pro Asp Asp Val Ala Tyr Gly Glu Ala Ser
            35                  40                  45

Lys Lys Thr Cys His Leu Met Ser Asn Ile Asn Ala Pro Lys Asp Leu
        50                  55                  60

Leu His Arg Ala Phe Ser Val Phe Leu Phe Arg Pro Ser Asp Gly Ala
    65                  70                  75                  80

Leu Leu Leu Gln Arg Arg Ala Asp Glu Lys Ile Thr Phe Pro Gly Met
                85                  90                  95

Trp Thr Asn Thr Cys Cys Ser His Pro Leu Ser Ile Lys Gly Glu Val
                100                 105                 110

Glu Glu Glu Asn Gln Ile Gly Val Arg Arg Ala Ala Ser Arg Lys Leu
```

```
                115                 120                 125
Glu His Glu Leu Gly Val Pro Thr Ser Ser Thr Pro Pro Asp Ser Phe
        130                 135                 140

Thr Tyr Leu Thr Arg Ile His Tyr Leu Ala Pro Ser Asp Gly Leu Trp
145                 150                 155                 160

Gly Glu His Glu Ile Asp Tyr Ile Leu Phe Ser Thr Thr Pro Thr Glu
                165                 170                 175

His Thr Gly Asn Pro Asn Glu Val Ser Asp Thr Arg Tyr Val Thr Lys
                    180                 185                 190

Pro Glu Leu Gln Ala Met Phe Glu Asp Glu Ser Asn Ser Phe Thr Pro
                195                 200                 205

Trp Phe Lys Leu Ile Ala Arg Asp Phe Leu Phe Gly Trp Trp Asp Gln
        210                 215                 220

Leu Leu Ala Arg Arg Asn Glu Lys Gly Glu Val Asp Ala Lys Ser Leu
225                 230                 235                 240

Glu Asp Leu Ser Asp Asn Lys Val Trp Lys Met
                245                 250
```

(2) INFORMATION FOR SEQ ID NO:2:

(i) SEQUENCE CHARACTERISTICS:
        (A) LENGTH: 259 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gln Leu Leu Ala Glu Asp Arg Thr Asp His Met Arg Gly Ala Ser
1               5                   10                  15

Thr Trp Ala Gly Gly Gln Ser Gln Asp Glu Leu Met Leu Lys Asp Glu
                20                  25                  30

Cys Ile Leu Val Asp Ala Asp Asn Ile Thr Gly His Val Ser Lys
            35                  40                  45

Leu Glu Cys His Lys Phe Leu Pro His Gln Pro Ala Gly Leu Leu His
    50                  55                  60

Arg Ala Phe Ser Val Phe Leu Phe Asp Asp Gln Gly Arg Leu Leu Leu
65                  70                  75                  80

Gln Gln Arg Ala Arg Ser Lys Ile Thr Phe Pro Ser Val Trp Thr Asn
                85                  90                  95

Thr Cys Cys Ser His Pro Leu His Gly Gln Thr Pro Asp Glu Val Asp
            100                 105                 110

Gln Leu Ser Gln Val Ala Asp Gly Thr Val Pro Gly Ala Lys Ala Ala
        115                 120                 125

Ala Ile Arg Lys Leu Glu His Glu Leu Gly Ile Pro Ala His Gln Leu
130                 135                 140

Pro Ala Ser Ala Phe Arg Phe Leu Thr Arg Leu His Tyr Cys Ala Ala
145                 150                 155                 160

Asp Val Gln Pro Ala Ala Thr Gln Ser Ala Leu Trp Gly Glu His Glu
                165                 170                 175

Met Asp Tyr Ile Leu Phe Ile Arg Ala Asn Val Thr Leu Ala Pro Asn
            180                 185                 190

Pro Asp Glu Val Asp Glu Val Arg Tyr Val Thr Gln Glu Glu Leu Arg
        195                 200                 205

Gln Met Met Gln Pro Asp Asn Gly Leu Gln Trp Ser Pro Trp Phe Arg
210                 215                 220
```

```
Ile Ile Ala Ala Arg Phe Leu Glu Arg Trp Trp Ala Asp Leu Asp Ala
225                 230                 235                 240

Ala Leu Asn Thr Asp Lys His Glu Asp Trp Gly Thr Val His His Ile
                245                 250                 255

Asn Glu Ala (2) INFORMATION FOR SEQ ID NO:3:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO:3:

Met Thr Ala Asp Asn Asn Ser Met Pro His Gly Ala Val Ser Ser Tyr
1               5                   10                  15

Ala Lys Leu Val Gln Asn Gln Thr Pro Glu Asp Ile Leu Glu Glu Phe
                20                  25                  30

Pro Glu Ile Ile Pro Leu Gln Gln Arg Pro Asn Thr Arg Ser Ser Glu
            35                  40                  45

Thr Ser Asn Asp Glu Ser Gly Glu Thr Cys Phe Ser Gly His Asp Glu
        50                  55                  60

Glu Gln Ile Lys Leu Met Asn Glu Asn Cys Ile Val Leu Asp Trp Asp
65                  70                  75                  80

Asp Asn Ala Ile Gly Ala Gly Thr Lys Lys Val Cys His Leu Met Glu
                85                  90                  95

Asn Ile Glu Lys Gly Leu Leu His Arg Ala Phe Ser Val Phe Ile Phe
                100                 105                 110

Asn Glu Gln Gly Glu Leu Leu Leu Gln Gln Arg Ala Thr Glu Lys Ile
                115                 120                 125

Thr Phe Pro Asp Leu Trp Thr Asn Thr Cys Cys Ser His Pro Leu Cys
130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
                165                 170                 175

Pro Glu Asp Glu Thr Lys Thr Arg Gly Lys Phe His Phe Leu Asn Arg
                180                 185                 190

Ile His Tyr Met Ala Pro Ser Asn Glu Pro Trp Gly Glu His Glu Ile
            195                 200                 205

Asp Tyr Ile Leu Phe Tyr Lys Ile Asn Ala Lys Glu Asn Leu Thr Val
        210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255

Phe Lys Ile Ile Cys Glu Asn Tyr Leu Phe Asn Trp Trp Glu Gln Leu
                260                 265                 270

Asp Asp Leu Ser Glu Val Glu Asn Asp Arg Gln Ile His Arg Met Leu
                275                 280                 285

(2) INFORMATION FOR SEQ ID NO:4:

(i) SEQUENCE CHARACTERISTICS:
```

(A) LENGTH: 1099 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 99..851

(xi) SEQUENCE DESCRIPTION: SEQ ID NO:4:

```
CCCACGCGTC CGCACATCTC GCATATATCA CTTTCCTCCT TCCAGAACAA GTTCTGAGTC      60

AACCGAAAAG AAAGAAGGCA GAGGAAAATA TATTCTAG ATG TCC ATG CCC AAC         113
                                          Met Ser Met Pro Asn
                                           1               5

ATT GTT CCC CCC GCC GAG GTC CGA ACC GAA GGA CTC AGT TTA GAA GAG       161
Ile Val Pro Pro Ala Glu Val Arg Thr Glu Gly Leu Ser Leu Glu Glu
               10                  15                  20

TAC GAT GAG GAG CAG GTC AGG CTG ATG GAG GAG CGA TGT ATT CTT GTT       209
Tyr Asp Glu Glu Gln Val Arg Leu Met Glu Glu Arg Cys Ile Leu Val
             25                  30                  35

AAC CCG GAC GAT GTG GCC TAT GGA GAG GCT TCG AAA AAG ACC TGC CAC       257
Asn Pro Asp Asp Val Ala Tyr Gly Glu Ala Ser Lys Lys Thr Cys His
         40                  45                  50

TTG ATG TCC AAC ATC AAC GCG CCC AAG GAC CTC CTC CAC CGA GCA TTC       305
Leu Met Ser Asn Ile Asn Ala Pro Lys Asp Leu Leu His Arg Ala Phe
     55                  60                  65

TCC GTG TTT CTC TTC CGC CCA TCG GAC GGA GCA CTC CTG CTT CAG CGA       353
Ser Val Phe Leu Phe Arg Pro Ser Asp Gly Ala Leu Leu Leu Gln Arg
 70                  75                  80                  85

AGA GCG GAC GAG AAG ATT ACG TTC CCT GGA ATG TGG ACC AAC ACG TGT       401
Arg Ala Asp Glu Lys Ile Thr Phe Pro Gly Met Trp Thr Asn Thr Cys
                 90                  95                 100

TGC AGT CAT CCT TTG AGC ATC AAG GGC GAG GTT GAA GAG GAG AAC CAG       449
Cys Ser His Pro Leu Ser Ile Lys Gly Glu Val Glu Glu Glu Asn Gln
             105                 110                 115

ATC GGT GTT CGA CGA GCT GCG TCC CGA AAG TTG GAG CAC GAG CTT GGC       497
Ile Gly Val Arg Arg Ala Ala Ser Arg Lys Leu Glu His Glu Leu Gly
         120                 125                 130

GTG CCT ACA TCG TCG ACT CCG CCC GAC TCG TTC ACC TAC CTC ACT AGG       545
Val Pro Thr Ser Ser Thr Pro Pro Asp Ser Phe Thr Tyr Leu Thr Arg
     135                 140                 145

ATA CAT TAC CTC GCT CCG AGT GAC GGA CTC TGG GGA GAA CAC GAG ATC       593
Ile His Tyr Leu Ala Pro Ser Asp Gly Leu Trp Gly Glu His Glu Ile
150                 155                 160                 165

GAC TAC ATT CTC TTC TCA ACC ACA CCT ACA GAA CAC ACT GGA AAC CCT       641
Asp Tyr Ile Leu Phe Ser Thr Thr Pro Thr Glu His Thr Gly Asn Pro
                 170                 175                 180

AAC GAA GTC TCT GAC ACT CGA TAT GTC ACC AAG CCC GAG CTC CAG GCG       689
Asn Glu Val Ser Asp Thr Arg Tyr Val Thr Lys Pro Glu Leu Gln Ala
             185                 190                 195

ATG TTT GAG GAC GAG TCT AAC TCA TTT ACC CCT TGG TTC AAG TTG ATT       737
Met Phe Glu Asp Glu Ser Asn Ser Phe Thr Pro Trp Phe Lys Leu Ile
         200                 205                 210

GCC CGA GAC TTC CTG TTT GGC TGG TGG GAT CAA CTT CTC GCC AGA CGA       785
Ala Arg Asp Phe Leu Phe Gly Trp Trp Asp Gln Leu Leu Ala Arg Arg
     215                 220                 225

AAT GAA AAG GGT GAG GTC GAT GCC AAA TCG TTG GAG GAT CTC TCG GAC       833
Asn Glu Lys Gly Glu Val Asp Ala Lys Ser Leu Glu Asp Leu Ser Asp
230                 235                 240                 245
```

```
AAC AAA GTC TGG AAG ATG TAGTCGACCC TTCTTTCTGT ACAGTCATCT              881
Asn Lys Val Trp Lys Met
                250

CAGTTCGCCT GTTGGTTGCT TGCTTCTTGC TCTTCTTTCT ATATATCTTT TTTCTTGCCT     941

GGGTAGACTT GATCTTTCTA CATAGCATAC GCATACATAC ATAAACTCTA TTTCTTGTTC    1001

TTTATCTCTC TTCTAAGGGA ATCTTCAAGA TCAATTTCTT TTTGGGCTAC AACATTTCAG    1061

ATCAATGTTG CTTTTCAGAC TACAAAAAAA AAAAAAAA                            1099

(2) INFORMATION FOR SEQ ID NO:5:

(i) SEQUENCE CHARACTERISTICS:
        (A) LENGTH: 1074 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 145..921

(xi) SEQUENCE DESCRIPTION: SEQ ID NO:5:

ATCGCTACTT GGAACCTGGC CCGGCGGCAG TCCGATGACG CGATGCTTCG TTCGTTGCTC      60

AGAGGCCTCA CGCATTTCCC CCGCGTGAAC TCCGCGCAGC AGCCCAGCTG TGCACACGCG     120

CGACTCCAGT TTAGGCCCAG AAGC ATG CAG CTG CTT GCC GAG GAC CGC ACA       171
                          Met Gln Leu Leu Ala Glu Asp Arg Thr
                            1               5

GAC CAT ATG AGG GGT GCA AGT ACC TGG GCA GGC GGG CAG TCG CAG GAT       219
Asp His Met Arg Gly Ala Ser Thr Trp Ala Gly Gly Gln Ser Gln Asp
 10              15                  20                  25

GAG CTG ATG CTG AAG GAC GAG TGC ATC TTG GTG GAT GCT GAC GAC AAC       267
Glu Leu Met Leu Lys Asp Glu Cys Ile Leu Val Asp Ala Asp Asp Asn
                 30                  35                  40

ATT ACA GGC CAT GTC AGC AAG CTG GAG TGC CAC AAG TTC CTA CCA CAT       315
Ile Thr Gly His Val Ser Lys Leu Glu Cys His Lys Phe Leu Pro His
             45                  50                  55

CAG CCT GCA GGC CTG CTG CAC CGG GCC TTC TCT GTA TTC CTG TTT GAC       363
Gln Pro Ala Gly Leu Leu His Arg Ala Phe Ser Val Phe Leu Phe Asp
         60                  65                  70

GAC CAG GGG CGA CTG CTG CTG CAA CAG CGT GCA CGA TCA AAA ATC ACA       411
Asp Gln Gly Arg Leu Leu Leu Gln Gln Arg Ala Arg Ser Lys Ile Thr
     75                  80                  85

TTC CCC AGT GTG TGG ACC AAC ACC TGC TGC AGC CAC CCT CTA CAT GGG       459
Phe Pro Ser Val Trp Thr Asn Thr Cys Cys Ser His Pro Leu His Gly
 90                  95                 100                 105

CAG ACC CCA GAT GAG GTG GAC CAA CTA AGC CAG GTG GCC GAC GGC ACA       507
Gln Thr Pro Asp Glu Val Asp Gln Leu Ser Gln Val Ala Asp Gly Thr
                110                 115                 120

GTA CCT GGC GCA AAG GCT GCT GCC ATC CGC AAG TTG GAG CAC GAG CTG       555
Val Pro Gly Ala Lys Ala Ala Ala Ile Arg Lys Leu Glu His Glu Leu
            125                 130                 135

GGG ATA CCA GCG CAC CAG CTG CCG GCC AGC GCG TTT CGC TTC CTC ACG       603
Gly Ile Pro Ala His Gln Leu Pro Ala Ser Ala Phe Arg Phe Leu Thr
        140                 145                 150

CGT TTG CAC TAC TGC GCC GCG GAC GTG CAG CCG GCT GCG ACA CAA TCA       651
Arg Leu His Tyr Cys Ala Ala Asp Val Gln Pro Ala Ala Thr Gln Ser
    155                 160                 165

GCA CTC TGG GGC GAG CAC GAA ATG GAC TAC ATC TTA TTC ATC CGG GCC       699
Ala Leu Trp Gly Glu His Glu Met Asp Tyr Ile Leu Phe Ile Arg Ala
```

-continued

```
                170                 175                 180                 185
AAC GTC ACC CTT GCG CCC AAC CCT GAC GAG GTG GAC GAA GTC AGG TAC      747
Asn Val Thr Leu Ala Pro Asn Pro Asp Glu Val Asp Glu Val Arg Tyr
                    190                 195                 200

GTG ACG CAG GAG GAG CTG CGG CAG ATG ATG CAG CCG GAC AAT GGG TTG      795
Val Thr Gln Glu Glu Leu Arg Gln Met Met Gln Pro Asp Asn Gly Leu
                205                 210                 215

CAA TGG TCG CCG TGG TTT CGC ATC ATC GCC GCG CGC TTC CTT GAG CGC      843
Gln Trp Ser Pro Trp Phe Arg Ile Ile Ala Ala Arg Phe Leu Glu Arg
            220                 225                 230

TGG TGG GCT GAC CTA GAC GCG GCC CTG AAC ACT GAC AAA CAC GAG GAT      891
Trp Trp Ala Asp Leu Asp Ala Ala Leu Asn Thr Asp Lys His Glu Asp
        235                 240                 245

TGG GGA ACG GTG CAT CAC ATC AAC GAA GCG TGAAAACAGA AGCTGTAGGA        941
Trp Gly Thr Val His His Ile Asn Glu Ala
250                 255

TGTCAAGACA CGTCATGAGG GGGCTTGGCA TCTTGGCGGC TTCGTATCTC TTTTTACTGA   1001

GACTGAACCT GCAGCTGGAG ACAATGGTGA GCCCAATTCA ACTTTCCGCT GCACTGGAAA   1061

AAAAAAAAAA AAA                                                     1074

(2) INFORMATION FOR SEQ ID NO:6:

(i) SEQUENCE CHARACTERISTICS:
        (A) LENGTH: 1058 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 187..1050

(xi) SEQUENCE DESCRIPTION: SEQ ID NO:6:

TCGATGGGGG TTGCCTTTCT TTTTCGGTCT TAACTCCATT TATATTTATT TATTCATTTT     60

TATCTATTTA ACAGGAAACA GTTTTCTAGT GACAAGAAGG CGTATATCCC ACTTAATTCA   120

ATATTAGAGT ATTCGTATTT GGAATACAGG AAGAGTAAAA ATAAGCCAAA AATTCATTAC   180

ACCTCA ATG ACT GCC GAC AAC AAT AGT ATG CCC CAT GGT GCA GTA TCT      228
       Met Thr Ala Asp Asn Asn Ser Met Pro His Gly Ala Val Ser
       1               5                   10

AGT TAC GCC AAA TTA GTG CAA AAC CAA ACA CCT GAA GAC ATT TTG GAA      276
Ser Tyr Ala Lys Leu Val Gln Asn Gln Thr Pro Glu Asp Ile Leu Glu
15              20                  25                  30

GAG TTT CCT GAA ATT ATT CCA TTA CAA CAA AGA CCT AAT ACC CGA TCT      324
Glu Phe Pro Glu Ile Ile Pro Leu Gln Gln Arg Pro Asn Thr Arg Ser
                35                  40                  45

AGT GAG ACG TCA AAT GAC GAA AGC GGA GAA ACA TGT TTT TCT GGT CAT      372
Ser Glu Thr Ser Asn Asp Glu Ser Gly Glu Thr Cys Phe Ser Gly His
            50                  55                  60

GAT GAG GAG CAA ATT AAG TTA ATG AAT GAA AAT TGT ATT GTT TTG GAT      420
Asp Glu Glu Gln Ile Lys Leu Met Asn Glu Asn Cys Ile Val Leu Asp
        65                  70                  75

TGG GAC GAT AAT GCT ATT GGT GCC GGT ACC AAG AAA GTT TGT CAT TTA      468
Trp Asp Asp Asn Ala Ile Gly Ala Gly Thr Lys Lys Val Cys His Leu
    80                  85                  90

ATG GAA AAT ATT GAA AAG GGT TTA CTA CAT CGT GCA TTC TCC GTC TTT      516
Met Glu Asn Ile Glu Lys Gly Leu Leu His Arg Ala Phe Ser Val Phe
95                  100                 105                 110
```

```
ATT TTC AAT GAA CAA GGT GAA TTA CTT TTA CAA CAA AGA GCC ACT GAA    564
Ile Phe Asn Glu Gln Gly Glu Leu Leu Leu Gln Gln Arg Ala Thr Glu
            115                 120                 125

AAA ATA ACT TTC CCT GAT CTT TGG ACT AAC ACA TGC TGC TCT CAT CCA    612
Lys Ile Thr Phe Pro Asp Leu Trp Thr Asn Thr Cys Cys Ser His Pro
        130                 135                 140

CTA TGT ATT GAT GAC GAA TTA GGT TTG AAG GGT AAG CTA GAC GAT AAG    660
Leu Cys Ile Asp Asp Glu Leu Gly Leu Lys Gly Lys Leu Asp Asp Lys
        145                 150                 155

ATT AAG GGC GCT ATT ACT GCG GCG GTG AGA AAA CTA GAT CAT GAA TTA    708
Ile Lys Gly Ala Ile Thr Ala Ala Val Arg Lys Leu Asp His Glu Leu
    160                 165                 170

GGT ATT CCA GAA GAT GAA ACT AAG ACA AGG GGT AAG TTT CAC TTT TTA    756
Gly Ile Pro Glu Asp Glu Thr Lys Thr Arg Gly Lys Phe His Phe Leu
175                 180                 185                 190

AAC AGA ATC CAT TAC ATG GCA CCA AGC AAT GAA CCA TGG GGT GAA CAT    804
Asn Arg Ile His Tyr Met Ala Pro Ser Asn Glu Pro Trp Gly Glu His
                195                 200                 205

GAA ATT GAT TAC ATC CTA TTT TAT AAG ATC AAC GCT AAA GAA AAC TTG    852
Glu Ile Asp Tyr Ile Leu Phe Tyr Lys Ile Asn Ala Lys Glu Asn Leu
            210                 215                 220

ACT GTC AAC CCA AAC GTC AAT GAA GTT AGA GAC TTC AAA TGG GTT TCA    900
Thr Val Asn Pro Asn Val Asn Glu Val Arg Asp Phe Lys Trp Val Ser
        225                 230                 235

CCA AAT GAT TTG AAA ACT ATG TTT GCT GAC CCA AGT TAC AAG TTT ACG    948
Pro Asn Asp Leu Lys Thr Met Phe Ala Asp Pro Ser Tyr Lys Phe Thr
        240                 245                 250

CCT TGG TTT AAG ATT ATT TGC GAG AAT TAC TTA TTC AAC TGG TGG GAG    996
Pro Trp Phe Lys Ile Ile Cys Glu Asn Tyr Leu Phe Asn Trp Trp Glu
255                 260                 265                 270

CAA TTA GAT GAC CTT TCT GAA GTG GAA AAT GAC AGG CAA ATT CAT AGA   1044
Gln Leu Asp Asp Leu Ser Glu Val Glu Asn Asp Arg Gln Ile His Arg
                275                 280                 285

ATG CTA TAACAACG                                                  1058
Met Leu (2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:7:

TCGATGGGGG TTGCCTTTCT TTTTCGG                                       27

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:8:

CGCGTTGTTA TAGCATTCTA TGAATTTGCC                                    30
```

METHODS OF PRODUCING CAROTENOIDS USING DNA MOLECULES ENCODING ISOPENTENYL PYROPHOSPHATE ISOMERASE

FIELD OF THE INVENTION

The present invention relates to a DNA chain which provides higher carotenoid content during biosynthesis of carotenoid and a method for producing carotenoids characterized by introducing said DNA chain into carotenoid producing microorganism to express said chain and to obtain higher carotenoid content.

BACKGROUND OF THE INVENTION

Carotenoid is a general name of a kind of natural pigments. Generally, carotenoids have 40 carbon atoms and consists of isoprene skeletons, and Carotenoids are abundant in the natural world. Approximately 600 kinds of carotenoids have been isolated and identified up to the present [(see Key to carotenoids. Basel-Boston, Birkhauser, 1987 (Pfander, H. ed.)]. Carotenoids are synthesized through the isoprenoid biosynthetic pathway, a part of which is common to the pathways for steroids and other terpenoids. Passing through the isoprene common biosynthetic pathway, hydroxymethylglutaryl-CoA(HMG-CoA) is converted to isopentenyl pyrophosphate(IPP), which has 5 carbon atoms, via mevalonate. Then IPP is converted to dimethylallyl pyrophosphate(DMAPP) by isomerization. Then, by polycondensation with IPP which has 5 carbon atoms, DMAPP is converted sequentially to geranyl pyrophosphate(GPP which has 10 carbon atoms), farnesyl pyrophosphate(FPP which has 15 carbon atoms), geranylgeranyl pyrophosphate (GGPP which has 20 carbon atoms) and so forth (FIG. 1).

The carotenoid biosynthetic pathway is branched from the isoprene common pathway at the point of GGPP is formed. At the point, two molecules of GGPP are condensed to synthesize phytoene which is the first carotenoid and colorless. Then, phytoene is converted to lycopene by desaturation reaction. Then, lycopene is converted to β-carotene by cyclization. Various xanthophylls such as zeaxanthin and astaxanthin are synthesized by introducing hydroxyl groups or keto groups to β-carotene.

Recently, the inventors of the present invention cloned the carotenoid biosynthesis genes derived from *Erwinia uredovora*, which is a non-photosynthetic epiphytic bacterium in *Escherichia coli* by using yellowish color of *Er. uredovora* as markers and elucidated the functions of the genes. Then, various combinations of these genes are introduced to express, and it made possible that microorganisms such as *E. coli* and yeast produce phytoene, lycopene, β-carotene, zeaxanthin and so forth(See FIG. 2): [See Misawa, N., Nakagawa, M., Kobayashi, K., Yamano, S., Izawa, Y., Nakamura, K. and Harashima, K., "Elucidation of the *Erwinia uredovora* carotenoid biosynthetic pathway by functional analysis of gene products expressed in *Escherichia coli*", J. Bacteriol., 172: 6704–6712 (1990); Misawa, N., Yamano, S., and Ikenaga, H., "Production of β-carotene in *Zymomonas mobilis* and *Agrobacterium tumefaciens* by introduction of the biosynthesis genes from *Erwinia uredovora*", Appl. Environ. Microbiol., 57: 1847–1849 (1991); Yamano, S., Ishii, T., Nakagawa, M., Ikenaga, H., and Misawa, N., "Metabolic engineering for production of β-carotene and lycopene in *Saccharomyces cerevisiae*", Biosci. Biotech. Biochem., 58: 1112–1114 (1994) and Japanese Patent Application laid-open No. HEI 3-58786 (Japanese Patent Application filing No. HEI 2-53255):"A DNA chain useful for synthesis of carotenoids" by the inventors of the present invention]. With the carotenoid biosynthesis genes from *Er. uredovora*, carotenoids can be synthesized from FPP. Since FPP is the common substrate not only for carotenoids but also for steroids and other terpenoids, bacteria incapable of synthesizing carotenoids also have FPP. Accordingly, for example, when four crt genes, crtE, crtB, crtI and crtY, which are necessary for biosynthesis of β-carotene from FPP are introduced in microorganisms, the microorganism becomes capable of producing β-carotene (See FIG. 2). Furthermore, by the same procedures as mentioned above, the inventors cloned the carotenoid biosynthesis genes derived from a marine bacterium, *Agrobacterium aurantiacum* in *E. coli*. By expressing various combinations of the genes from the bacterium and those from the above-mentioned *Er. uredovora*, it made possible that the microorganisms such as *E. coli* produce astaxanthin, canthaxanthin and so forth (See FIG. 3): (Norihiko Misawa et al., "Elucidation of an astaxanthin biosynthetic pathway at the level of the biosynthesis genes", Abstract of the 36th Symposium on the chemistry of natural products: 175–180 (1994)). Among the above carotenoids, astaxanthin, zeaxanthin and β-carotene are already in practical use and are regarded as promising substances. They are used for food or feed additives as red or yellow natural coloring agents or as nutritional aid having cancer prophylactic activity, immunopotentiating activity or provitamin A activity. Accordingly, when the carotenoid biosynthesis genes obtained by the inventors is used as exogenous genes for transforming microorganisms such as *E. coli* to express, it gave microorganisms such as *E. coli* the capability of biosynthesis for producing useful carotenoids. Up to now, it is the only way to improve production of useful carotenoids was to find out microorganism which can synthesize sufficient amount of a targeted carotenoid, and to try to increase its production by investigating culture conditions or mutation treatment. Owing to the studies done by the inventors, it became possible to choose host microorganism which is cultured easily and proliferates rapidly, and is guaranteed to be safe for food regardless of its carotenoid producing capability. As a matter of course, it is also possible to use microorganisms which can synthesize sufficient amount of useful carotenoids originally. In such a case, by transforming the microorganisms with carotenoid biosynthesis genes, it became possible to obtain higher carotenoid production or to alter final carotenoid products. For example, when both crtW and crtZ genes from *Ag. aurantiacum* were introduced into a microorganism capable of producing β-carotene as a final product to express them, the microorganism was transformed to another one which produce astaxanthin as a final product.

On the other hand, both astaxanthin and β-carotene can also be synthesized by organic synthesis methods. In these cases, considering these carotenoids are used for feed or food additives, there is problems that by-products are also produced and such synthetic products are not preferred by consumers because they prefer natural products. However, carotenoids produced by the conventional fermentation methods could not compete with those by the organic synthesis methods in price. As mentioned earlier, when the above mentioned carotenoid biosynthesis genes are used, it improves the fermentation methods, thereby it is considered that the carotenoid produced by the fermentation methods will be able to compete with those by the organic synthesis methods in price. If the microorganism can accumulate enough amount of carotenoid in itself, the carotenoid produced by the microorganisms will succeed in such price competition. Therefore, a technology to obtain higher carotenoid content by using microorganisms has been longed for.

Until now, in order to obtain higher carotenoid production in its biosynthesis; the traditional random mutation method is only employed to select mutant strains having higher carotenoid content with mutagenic agent such as NTG. However, this method requires huge amount of time and labor of technicians. In addition, even if enhancement of carotenoid synthesis is successfully achieved, the method requires both huge amount of time and effort to inhibit decreasing of carotenoid content caused by frequent reverse mutations naturally happens because the method lacks its theoretical basis.

SUMMARY OF THE INVENTION

The object of the present invention is to increase amount of carotenoids biosynthetically produced by microorganisms.

To solve the above problem, the inventors have investigated the problem thoroughly and developed a novel technology which provides several times higher carotenoid production amount by introducing a DNA chain containing only one gene into a carotenoid producing microorganism to express the gene in them.

More specifically, the inventors of the present invention found the followings and completed the present invention. When a DNA chain containing a gene substantially encoding an amino acid sequence of IPP isomerase which converts IPP into DMAPP, is introduced in microorganisms such as *E. coli* having carotenoid synthesis gene derived from *Er. uredovora* and so forth, content of carotenoid in cells such as lycopene and β-carotene becomes 1.5–4.5 times higher than that in control cells can be achieved. The gene substantially encoding IPP isomerase amino acid sequence which converts IPP into DMAPP was obtained from the astaxanthin producing microorganisms such as *Phaffia rhodozyma* and *Haematococcus pluvialis*.

The characteristics of the DNA chain of the present invention are as follows.
(1) A DNA chain capable of increasing carotenoid production amount and containing the nucleotide sequence which encodes the polypeptide having the amino acid sequence substantially shown in SEQ ID NO: 1, or a DNA chain that can be hybridized with said DNA chain.
(2) A DNA chain capable of increasing carotenoid production and containing the nucleotide sequence which encodes the polypeptide having the amino acid sequence substantially shown in SEQ ID NO:2, or a DNA chain that can be hybridized with said DNA chain.

The present invention also relates to a method for carotenoid production. The characteristics of the carotenoids production methods of the present invention are as follows.
(3) A production method characterized by introducing the DNA chain mentioned above either (1) or (2) into carotenoid producing microorganism, culturing said transformed microorganism and increasing carotenoid content in the cells and culture broth.
(4) A production method characterized by introducing the DNA chain containing the nucleotide sequence which encodes the polypeptide having the substantially same amino acid sequence shown in SEQ ID NO:3, or a DNA chain that can be hybridized with said DNA chain into carotenoid producing microorganism, culturing said microorganism and increasing carotenoid content in the cells and culture broth.

The present invention is described herein below.

As described in before, by introducing the carotenoid biosynthesis gene derived from microorganisms such as *Erwinia uredovora*, the non-photosynthetic soil bacteria and *Agrobacterium aurantiacum*, the marine bacteria) into other microorganisms which do not produce carotenoids such as *E. coli*, the microorganism can produce useful carotenoids such as astaxanthin, zeaxanthin, β-carotene and lycopene. In order to compete in price of the carotenoid produced by using the organic synthesis methods, it is necessary to achieve as higher carotenoid production as possible. The IPP isomerase gene, which include the gene encoding the polypeptide whose amino acid sequence is substantially IPP isomerase, of the invention is extremely useful for increasing the production amount of carotenoids. By using modern biotechnology, it is relatively easy to increase production amount of a protein encoded by an exogenous gene by enhancing expression level of the gene. However, if amounts of substrate necessary for a protein, that is enzyme, is limited, higher production of the protein does not lead to higher production of biochemicals such as carotenoids. For example, without sufficient amount of FPP, which is the first substrate, enhancement of expression level of the carotenoid synthesis genes does not lead to higher amount of carotenoids production. This time, we succeeded in increasing carotenoid production amount by introducing the IPP isomerase gene. It is considered that the introduction of the IPP isomerase gene makes the flow of, the upstream of the pathway up to FPP larger(more efficient) and consequently, increased supply of FPP led to higher carotenoid production amount. The present invention started from the findings that by introducing either the gene encoding IPP isomerase, which convert from IPP to DMAPP vise versa, or encoding the protein homologous to IPP isomerase into carotenoid producing microorganism such as *E. coli*, to express the gene, carotenoid production amount is increased. By using carotenoid biosynthesis genes from *Er. uredovora*, cDNA expression libraries of *Phaffia rhodozyma*, *Haematococcus pluvialis* and so forth were prepared in β-carotene producing *E. coli* as a host. As increased β-carotene content in *E. coli* made, some of the yellowish colonies brighter till almost orange. The plasmids extracted from such *E. coli* colonies were analyzed and were found to have genes with high homology to IPP isomerase of *Saccharomyces cerevisiae*. It has been speculated that HMG-CoA reductase(FIG. 1), which catalyzes the reaction from HMG-CoA to mevalonate, may be the rate limiting enzyme for terpenoids including carotenoids. However, as for IPP isomerase, any such report has not been presented. Therefore, increase of carotenoid production by introducing a IPP isomerase gene was a new finding.

The present invention provides a DNA chain having characteristics of increasing carotenoid production amount, and it containing the nucleotide sequence which encodes the polypeptide having the substantially same amino aid sequence as those of IPP isomerase, and a production method for carotenoid characterized by introducing said DNA chain into the carotenoid producing microorganism, culturing said transformed microorganism and increasing carotenoid content in the culture broth and cells.

The DNA chains of the present invention includes the DNA chains mentioned above (1) or (2), or the DNA chains which hybridize to said chains under stringent conditions.

Substantially, the polypeptides encoded by the DNA chains of the present invention have the amino acid sequences shown in SEQ ID NO:1 (A-B in FIGS. 4 and 5) or in SEQ ID NO:2 (C-D, in FIGS. 6 and 7). In the present invention, the polypeptides encoded by these DNA chains, the proteins of which amino acid sequence is substantially IPP isomerase, may be altered by deletion, replacement, addition and so forth of some amino acids, as long as the resulted polypeptides hold their higher carotenoid production activity. This allowance corresponds to "having the substantially same amino acid sequence substantially shown in SEQ ID NO:1 or SEQ ID NO:2". As an example, a sequence which lacks the first amino acid(Met) can be included as the altered polypeptide or the altered enzyme. Needless to say, the DNA chains of the present invention include not only the chains having the nucleotide sequences which encode the amino acid sequences shown in SEQ ID NOS 1 and 2 (FIGS. 4 to 5), but also the degenerate isomers of the chains, which differs only on degenerate codons and encode the same polypeptides as the original chains do.

(1) Obtaining the DNA Chains

One method to obtain a DNA chain having the nucleotide sequence which encodes the amino acid sequence of the above protein is chemical synthesis of the DNA chain at least a part of the chain according to the known nucleic acid synthesis method. However, considering that there are so many amino acids bound in the protein, it would be more preferable than chemical synthesis to make cDNA libraries of *Haematococcus pluvialis* or *Phaffia rhodozyma* or the like to obtain a targeted DNA chain by applying some popular method in the field of genetic engineering such as hybridization with appropriate probes.

(2) Transformation of Microorganisms Such As *E. coli* and Expression of Gene

Higher carotenoid content in culture broth or cells of microorganisms can be achieved by introducing the above mentioned DNA chain of the present invention into appropriate microorganisms such as carotenoid-producing bacteria such as *E. coli* and *Zymomonas mobilis* containing carotenoid biosynthesis genes from *Erwinia uredovora* and so forth, or carotenoid-producing yeast such as *Saccharomyces cerevisiae* containing carotenoid biosynthesis genes from *Erwinia uredovora* and so force.

The outline of the method to introduce exogenous genes into preferable microorganisms is mentioned below.

Procedures or methods to introduce and express exogenous genes in microorganisms such as *E. coli*, besides those mentioned below in the present invention, includes those widely used in the field of genetic engineering. Those are applicable to the invention. See "Vectors for cloning genes", Methods in Enzymology, 216: 469–631 (1992), Academic Press; "Other bacterial systems", Methods in Enzymology, 204: 305–636 (1991) Academic Press).

[*E. coli*]

There are some established and efficient methods to introduce exogenous genes to *E. coli* such as Hanahan's method and rubidium method, and they are applicable to the present invention (See Sambrook, J., Fritsch, E. F., Maniatis, T., "Molecular cloning—A laboratory manual", Cold Spring Harbor Laboratory Press (1989)). Expression of exogenous genes in *E. coli* can be performed by known methods (See "Molecular cloning—A laboratory manual", ibid.), for example, vectors for *E. coli* such as pUC and pBluescript vectors having lac promoter can be used. The inventors of the present invention used pSPORT1 vector or pBluescript II KS vector having lac promoter as vectors for *E. coli*, and inserted the IPP isomerase gene, derived from *Haematococcus pluvialis*, *Phaffia rhodozyma* or *Saccharomyces cerevisiae*, into the lac promoter with the direction of reading through of the transcription, and expressed the gene in *E. coli*.

[Yeast]

There are some established methods such as the lithium method to introduce exogenous genes into *Saccharomyces cerevisiae*, yeast, and such methods are applicable to the present invention (See "New biotechnology on yeast", Ed. Bio-industry Association(Yuichi Akiyama, editor in chief), Igaku Syuppan Center). Expression of exogenous genes in yeast can be performed as follows. Using both promoters and terminators, e.g. for PGK and GPD, an expression cassette is constructed by inserting the exogenous gene so that during transcription, the gene is to be read through at the position between the promoter and the terminator. Expression can be performed by inserting the expression cassette into a vector for *S. cerevisiae* such as YRp vectors (multi-copy vectors for yeast, replication starts at ARS sequence of yeast chromosome), YEp vectors (multi-copy vectors for yeast, replication starts at 2 μm DNA) and YIp vectors (vectors for yeast chromosome, no starting point of replication in yeast) (See "New biotechnology on yeast", ibid.; "Genetic engineering for production of substances", Ed. Japanese Society of Agricultural Chemistry, Asakura Publishing company; or Yamano, S., Ishii, T., Nakagawa, M., Ikenaga, H., Misawa, N., "Metabolic engineering for production of β-carotene and lycopene in *Saccharomyces cerevisiae*", Biosci. Biotech. Biochem., 58: 1112–1114 (1994)).

[*Zymomonas mobilis*]

Introduction of exogenous genes into *Zymomonas mobilis*, the ethanol-producing bacterium can be performed by conjugal transfer method which is commonly used for gram negative bacteria. Expression of exogenous gene in *Zymomonas mobilis* can be performed by using pZA22 vector for this bacterium (See Katsumi Nakamura, "Molecular breeding of Zymomonas bacteria", Journal of the Japanese Society of Agricultural Chemistry, 63: 1016–1018 (1989); and Misawa, N., Yamano, S., Ikenaga, H., "Production of β-carotene in *Zymomonas mobilis* and *Agrobacterium tumefaciens* by introduction of the biosynthesis genes from *Erwinia uredovora*", Appl. Environ. Microbiol., 57: 1847–1849 (1991)).

(3) Method to Increase Carotenoid Production in Microorganisms

By applying the above mentioned procedures or methods for introduction and expression of exogenous genes in microorganisms, both the carotenoid synthesis genes and the IPP isomerase gene can be introduced to express, and microorganisms capable of producing large amount of carotenoid can be obtained.

Farnesyl pyrophosphate (FPP) is the common substrate not only for carotenoids but also for other terpenoids such as sesquiterpenes, triterpenes, sterols and hopanols. In general, since microorganisms are synthesizing terpenoids even though they are not capable of synthesizing carotenoids, basically all of the microorganisms possesses FPP as an intermediate metabolite. On the other hand, *Erwinia uredovora*, the non-photosynthetic bacterium having the carotenoid synthesis genes can synthesize up to several useful carotenoids such as lycopene, β-carotene, zeaxanthin by using FPP as a substrate. When the genes are combined with the carotenoid synthesis genes of *Agrobacterium aurantiacum*, the marine bacterium, up to several useful carotenoids such as cantaxanthin and astaxanthin can also be synthesized (See FIGS. 2 and 3). The inventors of the present invention already confirmed that by introducing crt genes of *Erwinia uredovora* into microorganisms such as *Saccharomyces cerevisiae*, yeast and *Zymomonas mobilis*, ethanol-producing bacteria; these microorganisms can produce carotenoids such as β-carotene as anticipated [Yamano, S., Ishii, T., Nakagawa, M., Ikenaga, H., Misawa, N., "Metabolic engineering for production of β-carotene and lycopene in *Saccharomyces cerevisiae*", Biosci. Biotech. Biochem., 58:1112–1114 (1994); Misawa, N., Yamano, S., Ikenaga, H., "Production of β-carotene in *Zymomonas mobilis* and *Agrobacterium tumefaciens* by introduction of the biosynthesis genes from *Erwinia uredovora*", Appl. Environ. Microbiol., 57:1847–1849 (1991); and Japanese laid-open Patent Application No. HEI 3-58786(Japanese Patent Application filing No. HEI 2-53255):"A DNA chain useful for synthesis of carotenoids" by the inventors].

From the above findings, it can be expected that when an appropriate combinations of the carotenoid synthesis genes derived from *Er. uredovora* and those from marine bacteria (typically the carotenoid synthesis genes derived from *Ag. aurantiacum*) are introduced into the same microorganism simultaneously, as a principle, all of the microorganisms, in which such genes are introduced and of which introduction-expression system is established, can produce useful carotenoids such as astaxanthin and zeaxanthin.

In such cases, if the IPP isomerase gene(typically, derived from *Haematococcus pluvialis*, *Phaffia rhodozyma* and *Saccharomyces cerevisiae*) is introduced according to the above mentioned method, and is expressed concomitantly with the above carotenoid synthesis gene, higher production amount of useful carotenoids can be achieved.

(4) Deposit of the Microorganisms

The recombinant *E. coli* strain JM109 has been deposited as follows with the National Institute of Bioscience and Human-Technology, the Agency of Industrial Science and Technology. The strain contains the plasmid having the isolated gene which is the DNA chain of the invention. The names of the plasmids are shown in the parentheses.

(i) JM109(pRH1)

Deposit No.: FERM BP-5032

Date of Receipt: Mar. 6th, 1995

(ii) JM109(pHP11)

Deposit No.: FERM BP-5031

Date of Receipt: Mar. 6th, 1995

(ii) JM109(pSI1)

Deposit No.: FERM BP-5033

Date of Receipt: Mar. 6th, 1995

BRIEF DESCRIPTION OF THE DRAWINGS

FIGS. 4 and 5 show the coding nucleotide sequence of the IPP isomerase gene (SEQ ID NO:4) and the amino acid sequence (SEQ ID NO:1) of the polypeptide encoded by said gene of *Phaffia rhodozyma*, the astaxanthin-producing yeast. In the Figure, the sequence from mark A to B shows the open reading frame encoding the polypeptide consisting of 251 amino acids.

FIGS. 6 and 7 show the coding nucleotide sequence of the IPP isomerase gene (SEQ ID NO:5) and the amino acid sequence (SEQ ID NO:2) of the polypeptide encoded by said gene of *Haematococcus pluvialis*, the astaxanthin-producing green alga. In the Figure, the sequence from mark C to D shows the open reading frame encoding the polypeptide consisting of 259 amino acids.

FIGS. 8 and 9 show the coding nucleotide sequence of the IPP isomerase gene (SEQ ID NO:6) and the amino acid sequence (SEQ ID NO:3) of the polypeptide encoded by said gene of *Saccharomyces cerevisiae*, the yeast for laboratory use. In the Figure, the sequence from mark E to F shows the open reading frame encoding the polypeptide consisting 288 amino acids.

FIG. 14 shows production of lycopene(L:), β-carotene(β:) and phytoene(P:) in the cultured cells of the *E. coli* strains. In the Figure, "control" means the *E. coli* strain having no exogenous IPP isomerase gene.

EXAMPLE

Figure 1:
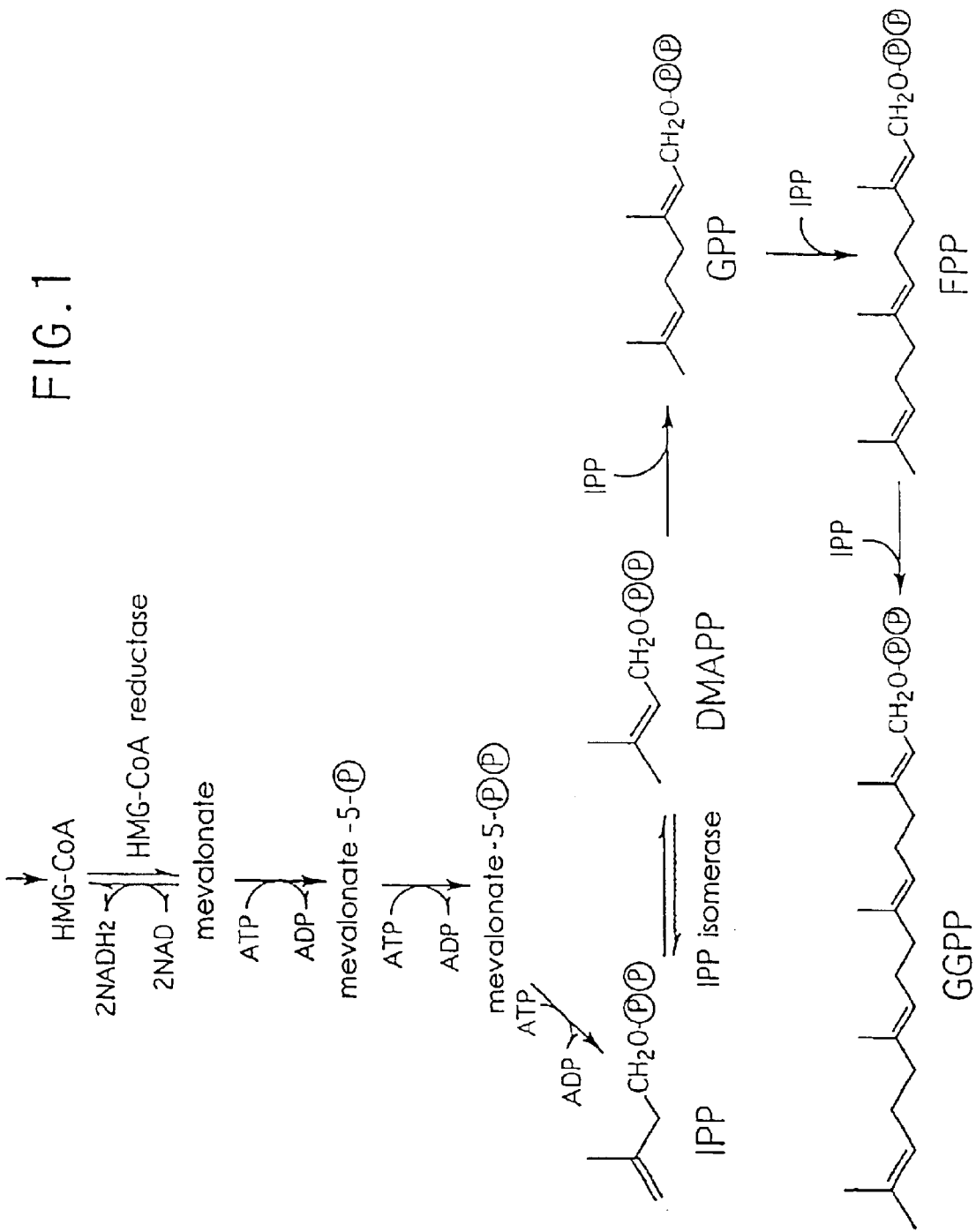
FIG. 1 shows the isoprene common biosynthetic pathway from HMG-CoA to FPP.

The following examples illustrate the present invention in more detail, however, the present invention is not limited to them. The genetic recombination experiments used here are based on the standard methods(Sambrook, J., Fritsch, E. F., Maniatis, T., "Molecular cloning—A laboratory manual", Cold spring Harbor Laboratory Press (1989)) unless otherwise stated.

EXAMPLE 1

Biological Materials and Culture Conditions

*Phaffia rhodozyma* ATCC 24230 strain(Astaxanthin-producing yeast) registered at the American Type Culture Collection(ATCC) is used. YM media(yeast extract 0.3%, malt extract 0.3%, bactopeptone 0.5%, Glucose 1%) is used for *Ph. rhodozyma*. *Haematococcus pluvialis*, the astaxanthin-producing green alga, NIES-144 strain registered at the Global Environmental Forum is used. *Ha. pluvialis* is cultured at 20° C. for about 4 days in basic culture media(yeast extract 0.2%, sodium acetate 0.12%, L-asparagin 0.04%, magnesium chloride hexahydrate 0.02%, ferrous sulfate heptahydrate 0.001%, calcium chloride dihydrate 0.002%) under 12 hr light(20 $\mu$E/m$^2$s)/12 hr dark condition. Furthermore, in order to induce astaxanthin synthesis in *Ha. pluvialis*, cyst formation, a kind of differentiation, has to be induced. To induce cyst formation, both acetic acid 45 mM and ferrous sulfate heptahydrate 450 $\mu$M at final concentrations are added. *Ha. pluvialis* in the media is cultured for about 12 hr at 20° C. with light(125 $\mu$E/m$^2$s). *Saccharomyces cerevisiae*(Yeast for laboratory use) S288C strain registered at the Yeast Genetic Stock Center is used. For *Sa. cerevisiae*, YPD media(yeast extract 1%, bactopeptone 2%, glucose 2%) is used.

EXAMPLE 2

Preparation of Whole RNA in *Phaffia rhodozyma*

*Phaffia rhodozyma* ATCC 24230 strain is cultured with shaking for approx. 24 hr at 20° C. in 400 ml of YM media.

When the turbidity of the media reached at OD600=0.4, the bacteria are collected and frozen in liquid nitrogen. The frozen bacteria are stored in the freezer at −80° C. and used for preparing total RNA. After thawing the frozen bacteria in a tube on ice, the bacteria are suspended in 6 ml of ANE buffer(10 mM sodium acetate, 100 mM sodium chloride, 1 mM EDTA, pH 6.0). Glass beads are added to cover the surface of the bacteria layer. Then, 600 µl of 10% SDS and 6 ml of phenol prewarmed at 65° C. are added. The suspension is kept at 65° C. for 5 minutes, and the tube is vortexed to crushed cell membranes at every 30 seconds. Then, the suspension is rapidly cooled down to room temperature and centrifuged for 10 minutes at 1,500×g at room temperature. Equal volume of phenol is added to the supernatant and vortex for 2 minutes. Then the suspension was centrifuged for 10 minutes at 1,500×g at room temperature. Then, by using equal volume of phenol/chloroform(1/1(v/v)) and chloroform alone, the same procedures as above are performed. To the resulted supernatant, one tenth volume of 3 M sodium acetate and three volume of ethanol are added; then the supernatant is stored in the freezer at −20° C. for 30 minutes. The supernatant is centrifuged for 15 minutes at 15,000×g at 4° C., a pellet is rinsed with 70% ethanol and dried. The residual is dissolved in 200 µl of sterilized water to make total RNA solution of *Ph. rhodozyma*. By this preparation procedure, 1.6 mg of total RNA is obtained.

EXAMPLE 3

Preparation of Whole RNA in *Haematococcus Pluvialis*

*Haematococcus pluvialis* NIES-144 strain is cultured for approx. 4 days in 800 ml of the basic culture media under the condition of 20° C., light intensity at 20 µE/m$^2$s and 12 hr light/12 hr dark cycle. Then, both acetic acid 45 mM and ferrous sulfate heptahydrate 450 µM as final concentrations are added. The *H. pluvialis* in the media is cultured for approx. 12 hr at 20° C. with light(125 µE/m$^2$s). The bacteria are collected from the media, frozen in liquid nitrogen and crushed in the mortar to give powder. Then, three ml of ISOGEN-LS[Nippon Gene K.K.] is added to the powder and stand for 5 minutes. Then 0.8 ml of chloroform is added, and the solution is stirred vigorously for 15 seconds and stand at room temperature for 3 minutes. The solution is centrifuged for 15 minutes at 4° C., 12,000×g, two ml of isopropanol is added to the supernatant and the supernatant is stood at room temperature for 10 minutes. Then, the solution is centrifuged for 10 minutes at 4° C., 12,000×g. The resulted pellet is rinsed with 70% ethanol to dry. After drying, the residual is dissolved in 1 ml of TE buffer(10 mM Tris-HCl pH 8.0, 1 mM EDTA) to make total RNA solution of *Ha. pluvialis*. By this preparation procedure, 4.1 mg of whole RNA was obtained.

EXAMPLE 4

Establishing cDNA Expression Libraries of *Phaffia rhodozyma* and *Haematococcus pluvialis*

By using Oligotex-dT30 Super[Takara Syuzo K.K.], poly A+RNA from *Phaffia rhodozyma* and *Haematococcus pluvialis* are purified from approx. 1 mg total RNA respectively. The purification is performed according to the methods mentioned in the package insert. By following the method, approx. 26 µg of poly A+mRNA from *Ph. rhodozyma* and approx. 14 µg of it from *Ha. pluvialis* are purified.

Preparation of cDNA is performed with Superscript™ plasmid system(GIBCO BRL) by the method mentioned in the package insert with some modifications. Approx. 5 µg of poly A+mRNA is used. A synthetic DNA consisting of the recognition sequence for the restriction enzyme NotI and 15 mers oligo-dT is used as a primer. The complementary DNA is synthesized with reverse transcriptase, SUPERSCRIPT RT. Then, by using *Escherichia coli* DNA ligase, *E. coli* DNA polymerase and *E. coli* RNase H, double strand DNA is synthesized. Then, the linker of the restriction enzyme SalI is bound by using T4 DNA ligase. cDNA is designed to have the SalI site at the upstream terminal of itself and the NotI site at the downstream of poly A. Fractionation by size of these cDNAs is performed by electrophoresis and the fractions ranging from 0.7 kb to 3.5 kb are collected. cDNA in the collected fractions is ligated to cDNA expression vector pSPORT I NotI-SalI-Cut by using both the ligation buffer which is included in the kit, 50 mM Tris-HCl pH 7.6, 10 mm MgCl$_2$, 1 mM ATP, 1 mM DTT, 5% PEG 8,000 and T4 DNA Ligase. The cDNA expression vector pSPORT I has lac promoter at the upstream of the SalI site and can express cDNA in *E. coli*. Then, by using whole the ligated DNA solution, transformation of the competent cells of *E. coli* DH5α prepared is performed according to the method described in "Molecular Cloning 2nd edition: Cold Spring Harbor Laboratory, 1.21–1.41(1989). Approx. 200,000 transformed strains of *Ph. rhodozyma* and approx. 40,000 transformed strains of *Ha. pluvialis* are obtained. After collecting all of the transformants, the plasmid DNA is prepared according to the method described in "Molecular Cloning 2nd edition, ibid." As a result, 0.9 mg and 0.6 mg of plasmid DNAs are obtained respectively and these are assigned as cDNA libraries of *Ph. rhodozyma* and *Ha. pluvialis*.

EXAMPLE 5

Preparation of Carotenoid-producing *E. coli*

Figure 10:
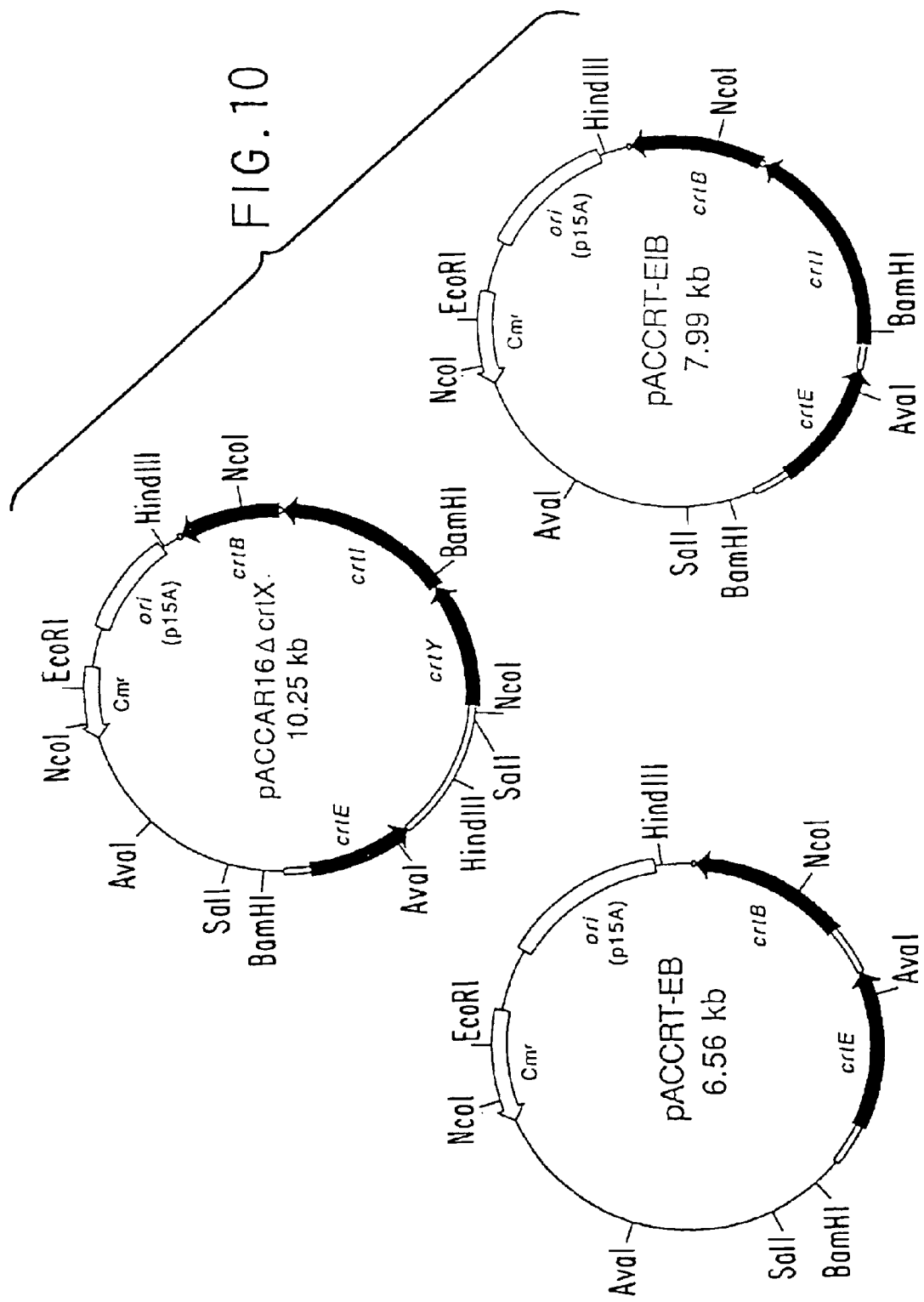
FIG. 10 shows the plasmids containing the carotenoid biosynthesis genes of *Erwinia uredovora*, the non-photosynthetic bacterium.

The plasmid pCAR16(Misawa, N., Nakagawa, M., Kobayashi, K., Yamano, S., Izawa, Y., Nakamura, K., Harashima, K., "Elucidation of the *Erwinia uredovora* carotenoid biosynthetic pathway by functional analysis of gene products expressed in *Escherichia coli*", J. Bacteriol., 172:p.6704–6712 (1990) and Japanese Patent Application laid-open No. HEI 3-58786 (Japanese Patent Application filing No. HEI 2-53255): "A DNA chain useful for synthesis of carotenoids" by the present inventors) having the carotenoid synthesis genes except for crtZ derived from *Erwinia uredovora*, is digested with BstEII, treated with Klenow enzyme and religated to inactivate the crtX gene by frame shift. After that, the 6.0 kb Asp718(KpnI)-ECoRI fragment containing crtE, crtB, crtI and crtY genes necessary for β-carotene production is taken out. The fragment is then inserted into the EcoRV sites of the *E. coli* vector pACYC184 and the desirable plasmid(named pACCAR16ΔcrtX, FIG. 10) is obtained. *E. coli* containing this plasmid (pACCAR16ΔcrtX) is chloramphenicol resistant and has yellowish color due to β-carotene production.

Then, the plasmid pCAR16 is digested with BstEII/SnaBI, treated with Klenow enzyme and religated to remove the 2.26 kb BstEII-SnaBI fragment containing crtX and crtY genes. After that, the 3.75 kb Asp718(KpnI)-EcoRI fragment containing crtE, crtB and crtI genes necessary for lycopene production is taken out. The fragment is then inserted into the EcoRV sites of the *E. coli* vector pACYC184 and the desirable plasmid(named pACCRT-EIB, FIG. 10) is obtained. *E. coli* containing pACCRT-EIB is chloramphenicol resistant and has reddish color due to lycopene production (Cunningham Jr., F. X., Chamovitz, D., Misawa, N., Gatt, E., Hirschberf, J., "Cloning and functional expression in *Escherichia coli* of a cyanobacterial gene for lycopene cyclase, the enzyme that catalyzes the biosynthesis of β-carotene", FEBS Lett., 328: 130–138 (1993)).

Figure 2:
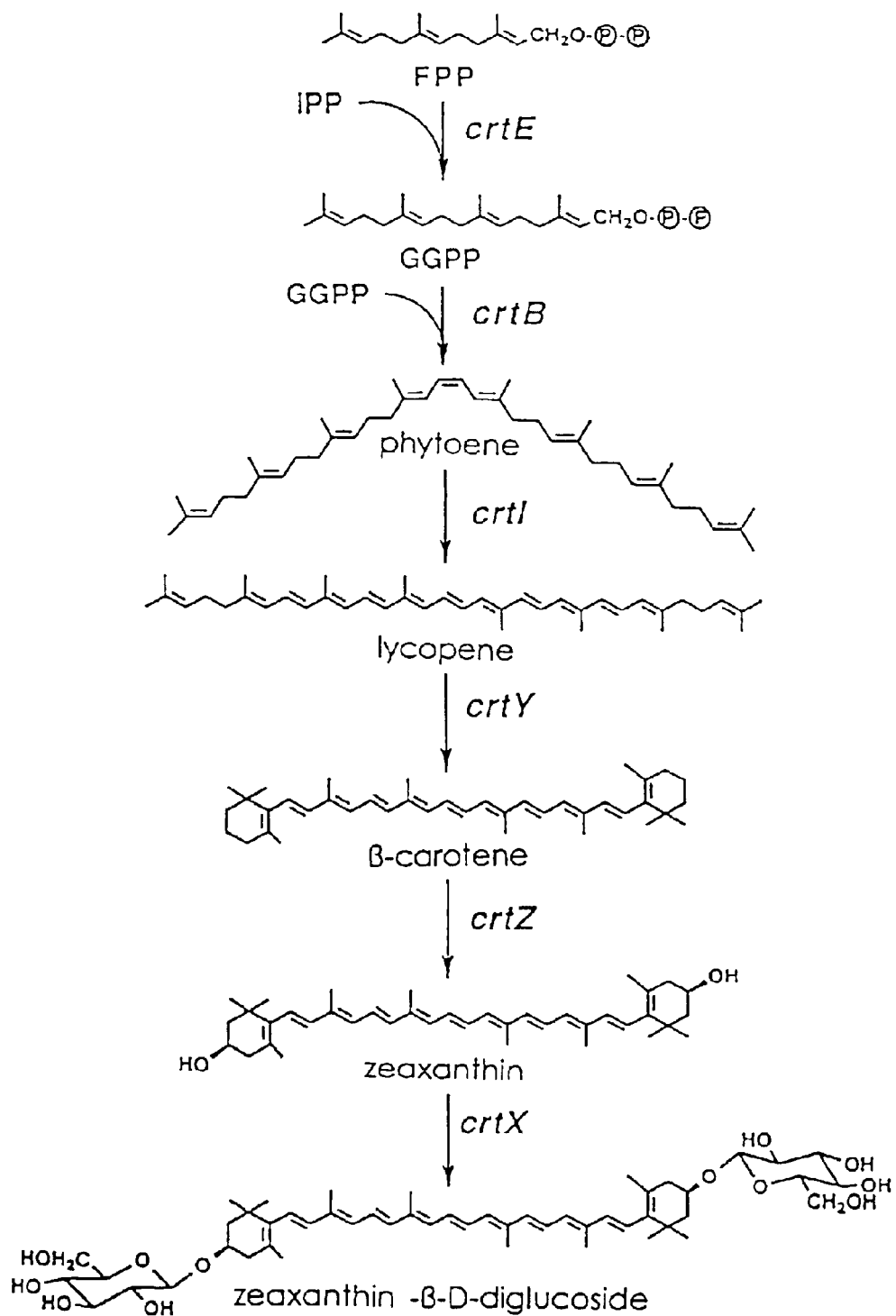
FIG. 2 shows the carotenoid biosynthetic pathway, and the functions of the carotenoid synthesis genes of *Erwinia uredovora*, the non-photosynthetic bacterium.
Figure 3:
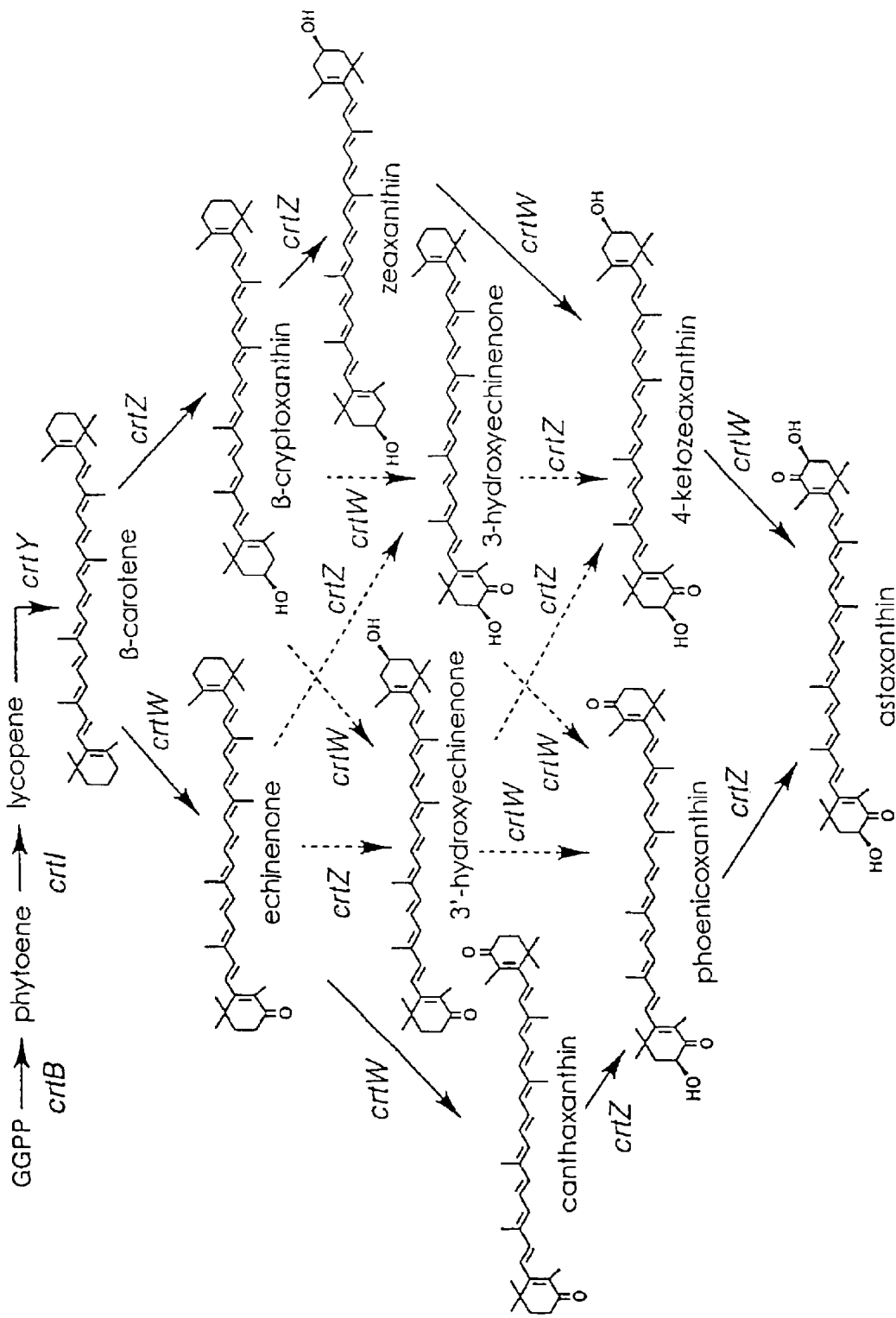
FIG. 3 shows the carotenoid biosynthetic pathway, and the functions of the carotenoid synthesis genes of *Agrobacterium aurantiacum*, the marine bacterium. The solid line shows major biosynthetic pathway and the dotted line shows minor one.

Then, the plasmid pCAR16 is digested with BstEII/Eco52I, treated with Klenow enzyme and religated to remove the 3.7 kb BstEII-Eco52I fragment containing crtX, crtY and crtI genes. After that, the 2.3 kb Asp718(KpnI)-EcoRI fragment containing crtE and crtB genes(FIG. 2) necessary for phytoene production is taken out. The fragment is then inserted into the EcoRV sites of the *E. coli* vector pACYC184 and the decibel plasmid(named pACCRT-EB, FIG. 10) is obtained. *E. coli* containing pACCRT-EB is chloramphenicol resistant and does not show color change as phytoene is colorless (Linden, H., Misawa, N., Chamovitz, D., Pecker, I., Hirschberg, J., Sandmann, G., "Functional complementation in *Escherichia coli* of different phytoene desaturase genes and analysis of accumulated carotenes", Z. Naturforsch. 46c: 1045–1051 (1991)).

EXAMPLE 6

Screening of Genes that Increase β-carotene Production

As the *E. coli* strain JM101 containing the above plasmid pACCAR16ΔcrtX shows yellowish color due to β-carotene production, it was investigated whether more yellowish transformant can be obtained by introducing cDNA expression library of *Phaffia rhodozyma* or *Haematococcus pluvialis*. As a first step, competent cells of *E. coli* JM101 containing pACCAR16ΔcrtX are prepared according to the method described in "Molecular cloning 2nd edition: Cold Spring Harbor Laboratory, 1.21–1.41(1989). Then, one hundred ng of each cDNA expression library of *Ph. rhodozyma* and *Ha. pluvialis* is introduced to 1 ml of the competent cells. Approx. 200,000 transformants of *Ph. rhodozyma* and approx. 40,000 transformants of *Ha. pluvialis* are obtained and inoculated for screening on the LB plate(bactotrypton 1%, yeast extract 0.5%, NaCl 1%, agar 1.5%) containing 150 μg/ml of ampicillin, 30 μg/ml of chloramphenicol and 1 mM of IPTG. From the screening, 5 strains of *Ph. rhodozyma* and 10 strains of *Ha. pluvialis* shows deep yellowish color than other strains and they are isolated. The plasmid DNA extracted from these strains is subject to restriction enzyme analysis, and it was found that the plasmids from the five strains and ten strains have common DNA fragment respectively. Of these screened plasmids derived from the cDNA expression libraries, a plasmid from *Ph. rhodozyma* was named pRH1(FIG. 11) and another plasmid from *Ha. pluvialis* was named pHP1. In addition to that, a fragment is taken out after digesting pHP1 with SalI and NotI, and then, the fragment is inserted into pBluescript KS+. The resulted plasmid was named pHP11(FIG. 11) and was used for the experiments mentioned below.

EXAMPLE 7

Nucleotide Sequence Determination on the Gene that Increases β-carotene Production From the plasmids pRH1 and pHP1, the deletion plasmids which lack various lengths from the original plasmids are prepared by the following procedures. By using those deletion plasmids, the nucleotide sequences are determined. Decomposition of pRP1 is performed with both ECoRI and PstI, or with both NotI and SphI. Decomposition of pHP1 is performed with both AatII and BamHI, or with both KpnI and EcoRI. After extraction with phenol/chloroform, DNA is recovered by ethanol precipitation. Each DNA fraction is then dissolved in 100 μl portions of ExoIII buffer(50 mM Tris-HCl, 100 mM NaCl, 5 mM MgCl$_2$, 10 mM2-mercaptoethanol, pH 8.0) and is kept at 37° C. after addition of 180 units of ExoIII nuclease. Ten μl portions of the solution are sampled every 30 seconds and transferred to tubes containing 10 μl of MB buffer(40 mM NaCl, 2 mM ZnCl$_2$, 10% glycerol, pH 4.5) in an ice bath. After sampling, the 10 tubes are kept at 65° C. for 10 minutes to inactivate the enzyme. Then, 5 units of mung bean nuclease is added and kept at 37° C. for 30 minutes. From one original plasmid, ten different kind of DNA fragments are recovered by agarose gel electrophoresis. The degree of deletion of each fragment varies. The terminals of the recovered DNAs are smoothed with Klenow enzyme to subject to ligation reaction at 16° C. overnight, and by using resulting DNA, *E. coli* DH5α is transformed to obtain clones. The plasmids are prepared from the various clones obtained, and nucleotide sequences are determined by using luminescence primer cycle sequence kit(Applied Biosystems corp.) with an automatic sequencer.

As a result, it was found that the nucleotide sequence of the cDNA in pRH1 derived from *Phaffia rhodozyma* consists of 1,099 base pairs (SEQ ID NO:4), and there is an open reading frame which encodes a polypeptide having 251 amino acids (SEQ ID NO:1) (which corresponds the region from A to B in FIGS. 4 and 5). It was also found that the nucleotide sequence of the cDNA in pHP1 derived from *Haematococcus pluvialis* consists of 1,074 base pairs (SEQ ID NO:5), and there is an open reading frame which encodes a polypeptide having 259 amino acids (SEQ ID NO:2) (which corresponds the region from C to D in FIGS. 6 and 7). The amino acid sequences expected from these open reading frames are investigated by analyzing homology in the Gene Bank. Both of the amino acid sequences of *Ph. rhodozyma* and *Ha. pluvialis* have significant homology with the IPP isomerase gene of *Saccharomyces cerevisiae*, 27.0% for *Ph. rhodozyma* and 20.3% for *Ha. pluvialis*. Therefore the genes were identified as the IPP isomerase gene.

EXAMPLE 8

Preparation of Total DNA in *Saccharomyces cerevisiae*

Preparation of total DNA in *Saccharomyces cerevisiae* is performed according to the method described in "Methods in Yeast Genetics; a laboratory course manual: Cold Spring Harbor Laboratory, p.131–132(1990). *Sa. cerevisiae* S288C strain is inoculated in 10 ml of YPD media and cultured at 30° C. overnight. The cultured cells are collected and suspended in 0.5 ml of sterilized water for washing. By discarding the supernatant, the yeast are collected again. A 0.2 ml of the mixture(2% Triton X-100, 1% SDS, 100 mM NaCl, 10 mM Tris-HCl(pH 8), 1 mM EDTA), 0.2 ml of phenol/chloroform/isoamylalcohol (25/24/1 (v/v/v)) and 0.3 g of glass beads are added. After vortex mix for 3–4 minutes, two hundred μl of TE buffer(10 mM Tris-HCl(pH 8), 1 mM EDTA) is added. Then the solution is centrifuged for 5 minutes, and the supernatant is transferred to another tube and 1 ml of ethanol is added. Then the solution is centrifuged again for 2 minutes. The resulted pellet is dissolved in 0.4 ml of TE buffer. Then, two μl of RNase A(10 mg/ml) is added and the solution is stood for 5 minutes at 37° C. Then, ten μl of 4 M ammonium acetate and 1 ml of ethanol are added.

After mixing well, the solution is centrifuged for 2 minutes and the resulted pellet is recovered. After drying the pellet, it was dissolved with 50 µl of TE buffer to have total DNA of *S. cerevisiae* S288C strain. By this preparation procedure, 3.4 µg of total DNA was obtained.

EXAMPLE 9

Isolation of the IPP Isomerase Gene of *Saccharomyces cerevisiae* by PCR Method Based on the nucleotide sequence of the IPP isomerase gene of *S. cerevisiae* reported in the aforementioned reference(Anderson, M. S., Muehlbacher, M., Street, I. P., Profitt, J., Poulter, C. D., "Isopentenyl diphosphate: dimethylallyl diphosphate isomerase—an improved purification of the enzyme and isolation of the gene from *Saccharomyces cerevisiae*", J. Biol. Chem., 264:19169–19175(1989)), the primers (SEQ ID NOS. 7 and 8, respectively) below were synesized.

Primer No. 1 5'-TCGATGGGGGTTGCCTTTCTTTTTCGG-3'

Primer No. 2 5'-CGCGTTGTTATAGCATTCTATGAATTTGCC-3'

Figure 11:
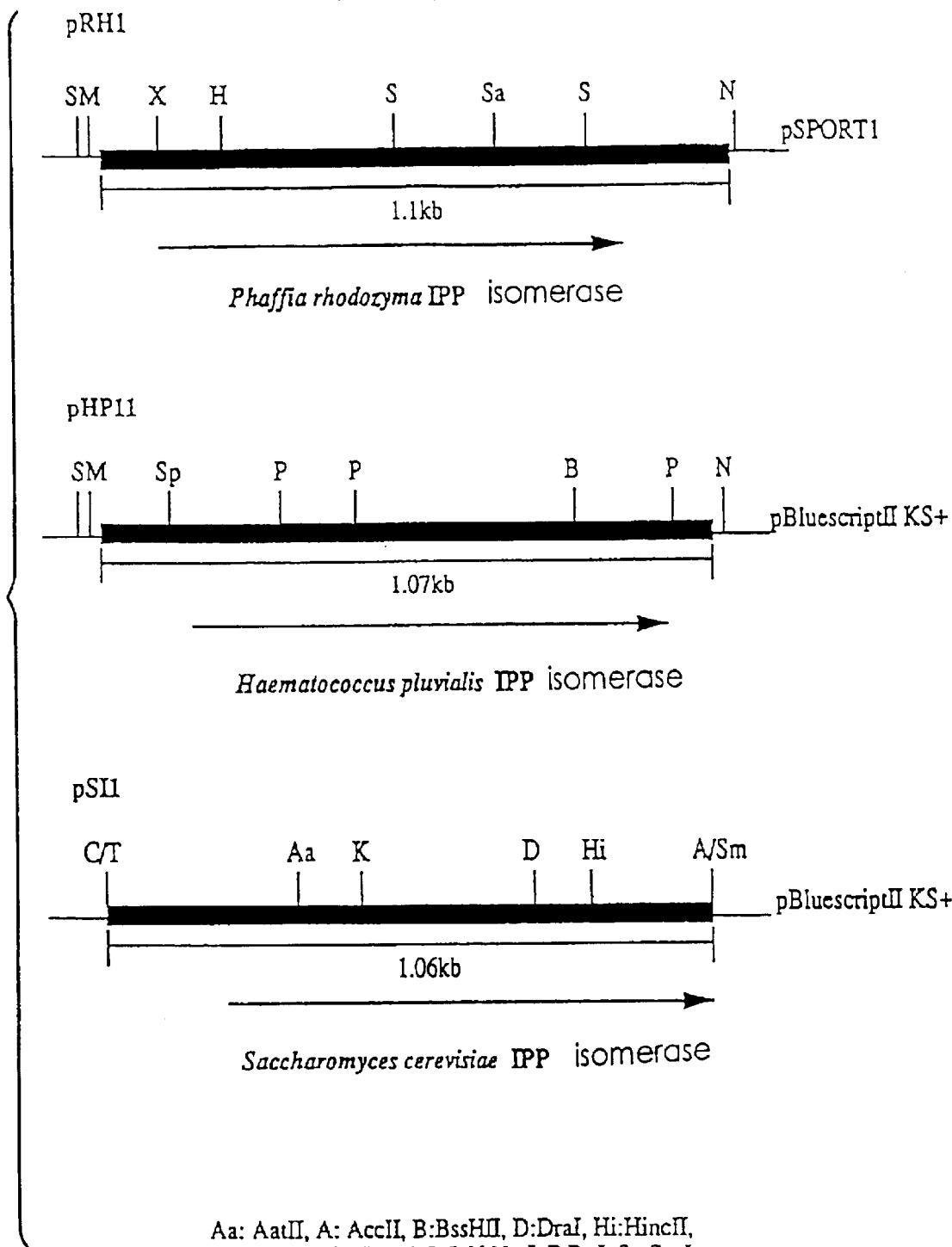
FIG. 11 shows the plasmids containing the IPP isomerase gene of *Phaffia rhodozyma*, *Haematococcus pluvialis*, or *Saccharomyces cerevisiae*.

The procedure was designed to obtain PCR amplified IPP isomerase gene having TaqI sites at the upstream terminal and AccII region at the downstream terminal. Thirty cycles of PCR is performed with 200 ng of total DNA of *S. cerevisiae* and PfuDNA polymerase (STRATAGENE). To express the IPP isomerase gene obtained by PCR in *E. coli*, it is digested with both TaqI and AccII. Then, the gene was inserted into ClaI sites and SmaI sites of pBluescript KS+ vector. The resulted plasmid was named pSI1(FIG. 11). This DNA derived from *S. cerevisiae* had a nucleotide sequence consisting of 1,058 bp (SEQ ID NO:6), and contained a gene which encodes IPP isomerase consisting of 288 amino acids (SEQ ID NO:3)(corresponds from E to F in FIGS. 8 and 9).

EXAMPLE 10

Increase of Lycopene Production Amount by Introducing the IPP Isomerase Gene Into the lycopene-producing *E. coli* JM101 strain (abbreviated as L hereafter) which contains pACCRT-EIB (FIG. 10), pSPORT1 vector, pRH1 plasmid containing the IPP isomerase gene of *Phaffia rhodozyma*, pHP11 plasmid containing the IPP isomerase gene of *Haematococcus pluvialis* or pSI1 plasmid containing the IPP isomerase gene of *Saccharomyces cerevisiae*(FIG. 11) are introduced respectively. These *E. coli* transformants are then plated on the LB plate containing 150 µg/ml of ampicillin (Ap), 30 µg/ml of chloramphenicol(Cm) and 1 mM of IPTG, and cultured at 28° C. overnight. The three strains, in which each IPP isomerase gene were introduced, showed deep reddish color due to lycopene production compared with the control (lycopene-producing *E.coli*) in which only vector is introduced. Furthermore, growth rate of the three strains on agar plates were faster than the control strains and they always showed larger colonies than those of the control during culture. It is considered that due to introduction and expression of the IPP isomerase gene, the upstream of the biosynthetic pathway up to FPP became more efficient(see FIG. 1), and consequently, increase of FPP supply led to increase of lycopene. As for faster growth rate, it is also considered that due to increase of FPP, sufficient amount of the substrate can be supplied not only for lycopene production but also for the production of other membrane components derived from FPP, that is, FPP or GGPP binding protein, and these components are necessary for growth of *E. coli*.

Figure 12:
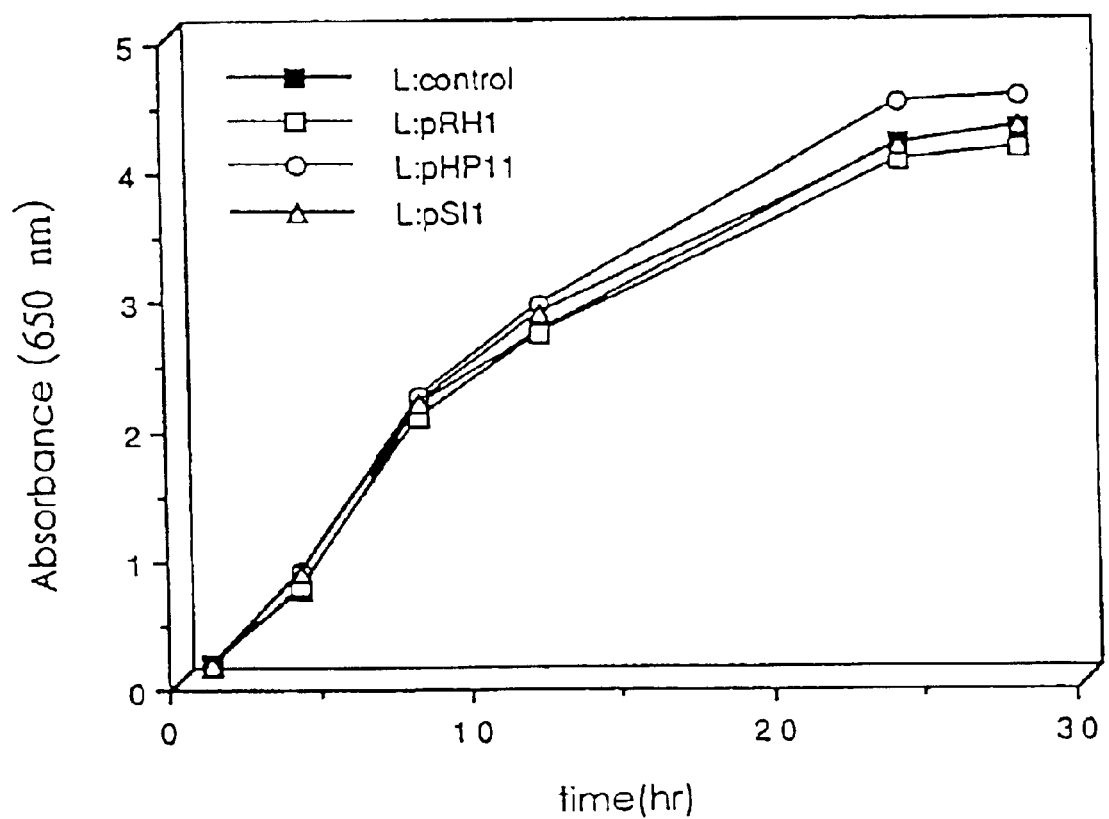
FIG. 12 shows the growth curve in the culture broth of the lycopene producing *E. coli* strains(L:). In the Figure, "control" means the *E. coli* strain having no exogenous IPP isomerase gene.
Figure 13:
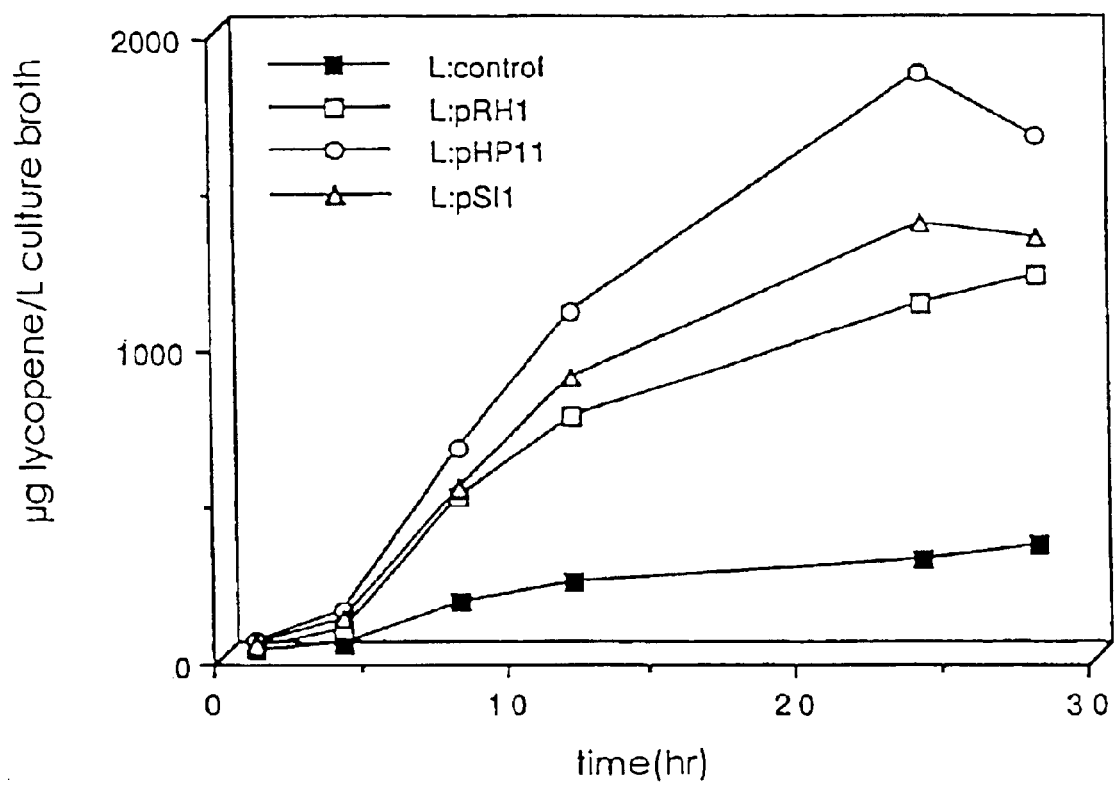
FIG. 13 shows the lycopene production curve in the culture broth of the lycopene producing *E. coli* strains(L:). In the Figure, "control" means the *E. coli* strain having no exogenous IPP isomerase gene.

Increase of lycopene production amount by *E.coli* carrying the IPP isomerase gene is also confirmed by liquid culture. After overnight shaking culture of the LB media(5 ml) containing both Ap and Cm at 28° C., 2 ml of the media is taken and transferred to 200 ml of 2YT culture media (1.6% bactotrypton, 1% yeast extract, 0.5% NaCl) containing Ap, Cp and 0.1 mM IPTG, and shaking culture is performed at 230 rpm, 28° C. Five ml each of the media is sampled several hours' intervals to determine growth rate and lycopene content. Growth rate is calculated from absorbance at 650 nm. Lycopene content is determined according to the following procedure. The cells collected by centrifugation, 2.5 ml of acetone is added to the cells and stand for 30 minutes. Vortex mix once in a while. After filtration, absorbance at 474 nm is measured to determine the lycopene content based on the absorbance 185.0 for 1 mM lycopene (light path: 1 cm). JASCO UVIDEC-220B spectrophotometer is used. By using HPLC, it is confirmed that these strains actually produced lycopene and absorbance at 474 nm is attributable to lycopene. HPLC conditions are mentioned in EXAMPLE 11. The results are shown in FIG. 12(growth curve) and FIG. 13(lycopene production curve). As for the growth rate(FIG. 12), there is no difference among any the strains including the control strains. This result is different from that obtained from culture plates. Probably, when the liquid culture is performed, even in the control strain which does not have exogenous IPP isomerase gene can grow rapidly, because the supply of the substrate for membrane components such as FPP and GGPP binding protein is enough compared to agar culture is done. In contrast, there is a big difference between the control strain having no exogenous IPP isomerase gene and the three exogenous IPP isomerase gene-carrying strains. During culture, the three strains always showed several times higher lycopene production amount compared with the control strain. Lycopene production amount per *E. coli* dry weight at 28 hr after the start of the culture is shown in FIG. 14. The three strains containing the IPP isomerase gene showed 3.6–4.5 times higher production than the control strain. Lycopene-producing *E. coli* containing pHP11 is able to produce 1.03 mg lycopene per 1 g dry weight.

EXAMPLE 11

Increase of β-carotene Production Amount by Introducing the IPP Isomerase Gene Into the β-carotene producing *E. coli* JM101 strain (abbreviated as β hereafter) which contains pACCAR16ΔcrtX(FIG. 10), either pSPORT1 vector or pRH1 plasmid containing the IPP isomerase gene of *Phaffia rhodozyma* is introduced separately. After overnight shaking culture of the LB media(5 ml) containing both Ap and Cm at 28° C., 1 ml of the media is taken and transferred to 100 ml of 2YT media containing Ap, Cm and 0.1 mM IPTG, and shaking culture is performed at 230 rpm at 28° C. for 28 hr. The bacteria are collected by centrifugation and washed with 0.85% NaCl. After washing, the bacteria are suspended in 40 ml of acetone and allowed to stand for 30 minutes. Vortex mix once in a while. After filtration, absorbance at 454 nm is measured to determine β-carotene content based on the absorbance 134.4 for 1 mM β-carotene (light path: 1 cm). The result is shown in FIG. 14. β-Carotene producing *E. coli* containing pRH1 produced 709 µg of β-carotene per 1 g dry weight. This amount is 1.5 times higher than the control.

By using HPLC on the above acetone extract, it is confirmed that these strains actually produced β-carotene and absorbance at 454 nm is attributable to β-carotene. Novapack HR 6μ C18(3.9×300 mm, Waters) is used as a column. Acetonitrile/methanol/2-propanol(90/6/4(v/v/v)) is used as an elution solvent. A photodiode array detector 996(Waters) is used to monitor an elution profile. The results showed that almost 100% of a peak appeared in a visible spectrum is β-carotene. As the β-carotene standard preparation, chemically synthesized β-carotene (Sigma) is used.

EXAMPLE 12

Increase of Phytoene Production Amount by Introducing the IPP Isomerase Gene Into the phytoene producing *E. coli* JM101 strain (abbreviated as P hereafter) which contains pACCRT-EB (FIG. 10), any of pSPORT1 vector, pRH1 plasmid containing the IPP isomerase gene of *Phaffia rhodozyma* or pHP11 plasmid containing the IPP isomerase gene of *Haematococcus pluvialis* is introduced separately. After overnight shaking culture of the LB media(5 ml) containing both Ap and Cm at 28° C., 1 ml of the media is taken and transferred to 100 ml of 2YT media containing Ap, Cm and 0.1 mM IPTG, and shaking culture is performed at 230 rpm at 28° C. for 28 hr. The bacteria are collected by centrifugation and washed with 0.85% NaCl. After washing, the bacteria are suspended in 40 ml of acetone and allowed to stand for 30 minutes. Vortex mix once in a while. After filtration and drying by rotary evaporator, partition is performed with 40 ml of petroleum ether and water. Absorbance of the ether layer at 286 nm is measured to determine phytoene content based on the absorbance 41.2 for 1 mM phytoene (light path: 1 cm). As HPLC analysis described in EXAMPLE 11 showed that 70% of the absorbance at 286 nm is attributable to phytoene, an and also actual phytoene content is adjusted to 70% of the above value. The result is shown in FIG. 14. Phytoene-producing *E. coli* containing the IPP isomerase gene produced 1.7–2.1 times higher phytoene than control strain.

From the above examples, we showed that by introducing the IPP isomerase gene into β-carotene, lycopene or phytoene-producing *E. coli,* several times higher carotenoid production is actually achieved. It is considered that due to introduction and expression of the IPP isomerase gene, upstream of the biosynthetic pathway up to FPP became more efficient(see FIG. 1), and consequently, increase of FPP supply led to increase of these carotenoids. Therefore, it is considered that this findings can be applicable not only for β-carotene, lycopene and phytoene productions but also for all other carotenoids such as astaxanthin and zeaxanthin.

The present invention provides a DNA chain which can significantly increase carotenoid production in biosynthesis of carotenoid by microorganisms and a method to obtain several times higher carotenoid production amount by introducing and expressing said DNA chain into carotenoid-producing microorganisms. It is expected that said DNA chain can be applicable to increase production in microorganisms not only for carotenoids but also for terpenoids and so forth which require same substrate(FPP) as carotenoids.

What is claimed is:

1. A method for producing carotenoids comprising:
   a) transforming a DNA molecule containing a nucleotide sequence that encodes a polypeptide comprising the amino acid sequence set forth in SEQ ID NO:1 or SEQ ID NO:2 into a carotenoid-producing microorganism,
   b) culturing said transformed microorganism, and
   c) obtaining carotenoids in the culture broth or cells.

2. A method according to claim 1, wherein said nucleotide sequence comprises SEQ ID NOs:4 or 5.

3. An isolated and purified DNA molecule comprising a nucleotide sequence encoding SEQ ID NO:1, which is the amino acid sequence of isopentenyl pyrophosphate isomerase from *Phaffia rhodozyma*.

4. An isolated and purified DNA molecule comprising a nucleotide sequence encoding SEQ ID NO:2, which is the amino acid sequence of isopentenyl pyrophosphate isomerase from *Haematococcus pluvialis*.

5. An isolated and purified DNA molecule according to claim 3, wherein said nucleotide sequence comprises SEQ ID NO:4.

6. An isolated and purified DNA molecule according to claim 4, wherein said nucleotide sequence comprises SEQ ID NO:5.

7. An isolated polypeptide comprising the amino acid sequence set forth in SEQ ID NO:1.

8. An isolated polypeptide comprising the amino acid sequence set forth in SEQ ID NO:2.

* * * * *